(12) United States Patent
Stratbucker

(10) Patent No.: US 6,532,379 B2
(45) Date of Patent: Mar. 11, 2003

(54) BIO-ELECTIC INTERFACE ADAPTER WITH TWELVE-LEAD ECG CAPABILITY AND PROVISION FOR DEFIBRILLATION

(76) Inventor: Robert A. Stratbucker, 7125 Country Club Rd., Omaha, NE (US) 68152

(*) Notice: Subject to any disclaimer, the term of this patent is extended or adjusted under 35 U.S.C. 154(b) by 52 days.

(21) Appl. No.: 09/777,296

(22) Filed: Feb. 6, 2001

(65) Prior Publication Data

US 2001/0027270 A1 Oct. 4, 2001

Related U.S. Application Data

(63) Continuation-in-part of application No. 09/374,873, filed on Aug. 16, 1999, now Pat. No. 6,327,487, which is a continuation-in-part of application No. 08/885,690, filed on Jun. 30, 1997, now Pat. No. 5,938,597, which is a continuation-in-part of application No. 08/434,658, filed on May 4, 1995, now Pat. No. 5,678,545.
(60) Provisional application No. 60/180,794, filed on Feb. 7, 2000.

(51) Int. Cl.[7] .................. A61B 5/0408; A61N 1/04; A61N 1/39
(52) U.S. Cl. .................. 600/382; 600/390; 600/391; 600/393; 607/142; 607/149; 607/152
(58) Field of Search ................ 600/372, 382, 600/388–391, 393; 607/142, 148, 149, 152

(56) References Cited

U.S. PATENT DOCUMENTS

| | | | | | |
|---|---|---|---|---|---|
| 4,072,145 | A | * | 2/1978 | Silva | 600/383 |
| 4,763,660 | A | * | 8/1988 | Kroll et al. | 600/391 |
| 5,078,134 | A | * | 1/1992 | Heilman et al. | 607/142 |
| 5,237,995 | A | * | 8/1993 | Cano | 600/397 |
| 6,065,154 | A | * | 5/2000 | Hulings et al. | 600/393 |
| 6,178,357 | B1 | * | 1/2001 | Gliner et al. | 600/392 |
| 6,400,975 | B1 | * | 6/2002 | McFee | 600/372 |

* cited by examiner

Primary Examiner—Lee Cohen
(74) Attorney, Agent, or Firm—James D. Welch

(57) ABSTRACT

Disclosed is a bio-electic interface adapter with at least two large area defibrilation electrodes and sufficient smaller precordial electrodes present therein to allow standard twelve lead ECG monitoring. The defibrillation electrodes can be affixed to the bioelectric interface via perforations, or by a functionally similar approach, to allow easy detachment in use. The bioelectric interface adaptor preferably has an undulated outer edge geometry, and provides electrodes for forming limb leads, optionally allowing use of the defibrillation electrodes as Right Arm and Left Leg electrodes. Limb lead forming electrodes are preferable affixed via perforations, or by a functionally similar approach, to allow easy detachment and deployment to conventional limb electrode locations, in use.

48 Claims, 14 Drawing Sheets

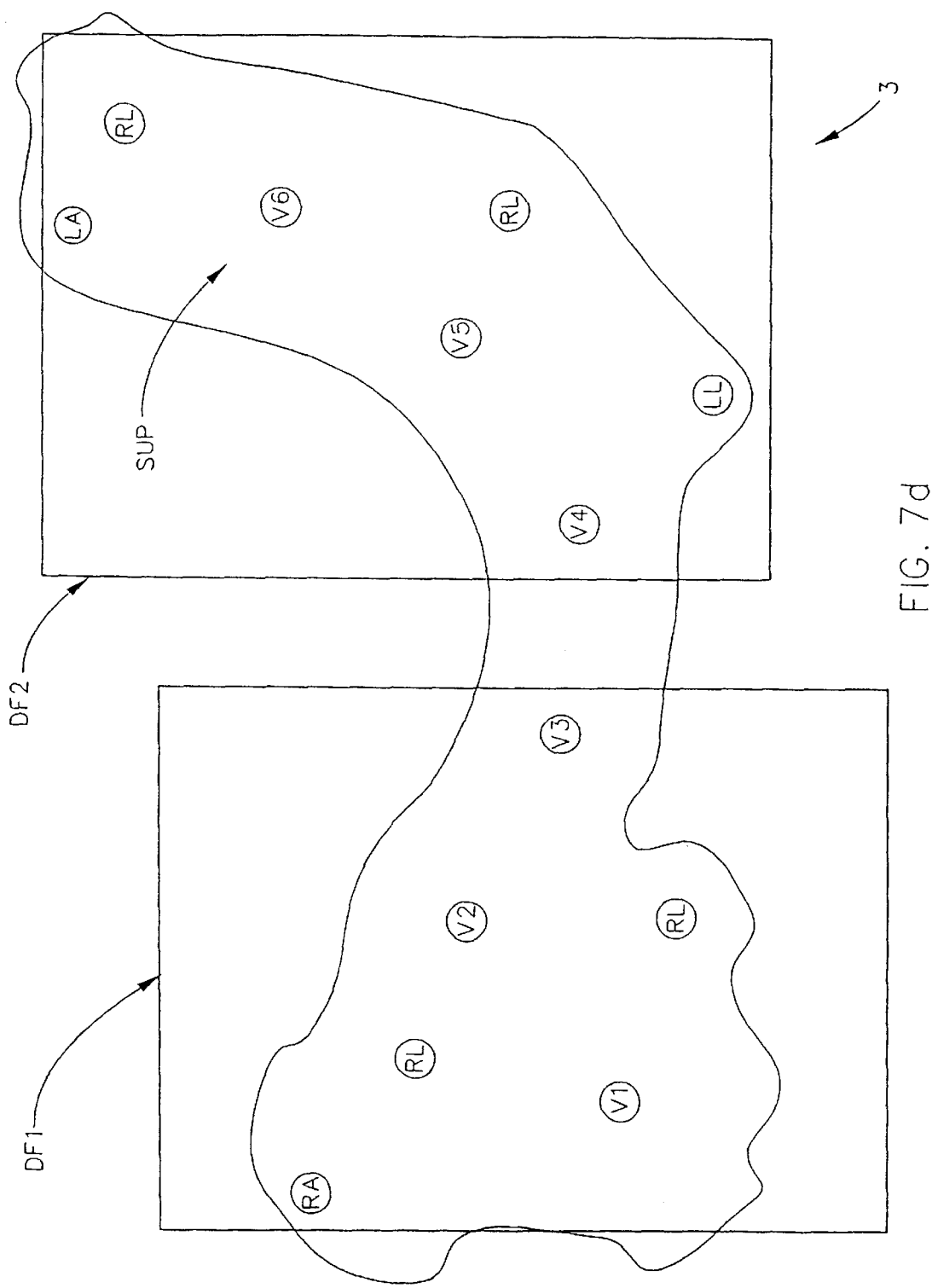

BIO-ELECTIC INTERFACE ADAPTER WITH TWELVE-LEAD ECG CAPABILITY AND PROVISION FOR DEFIBRILLATION

This application is a CIP of patent application Ser. No. 09/374,873 filed Aug. 16, 1999, now U.S. Pat. No. 6,327,487, which was a CIP of patent application Ser. No. 08/885,690 filed Jun. 30, 1997, now U.S. Pat. No. 5,938,597, which was a CIP of patent application Ser. No. 08/434,658 filed May 4, 1995, now U.S. Pat. No. 5,678,545, and is further a CIP of Provisional Application No. 60/180,794 filed Feb. 7, 2000.

TECHNICAL FILED

The present invention is related to chest-patch bio-electic interface adapters and more specifically, in its preferred embodiment, to a bio-electic interface adapter comprising safe and effective large area defibrillation electrodes in functional combination with sufficient additional precordial electrodes to allow multiple lead ECG monitoring, including international standard twelve lead monitoring, said defibrillation electrodes being optionally employed as Right Arm and Left Leg electrodes.

BACKGROUND

Conventional medical analysis and therapy often involves use of a plurality of individual electrodes, each applied independently to an appropriate location on a subject's body by way of electrically conductive paste, and securing means such as a skin compatible adhesive. A relevant example of use is in the monitoring of Electrocardiogram (ECG) signals at precordial; and at left and right arm, and left Leg locations by independent electrodes in an Einthoven triangle configuration.

Further, it is known to apply individual non-invasive precordial electrodes to a subject's chest to allow not only the acquiring of ECG data, but to allow administration of therapy, such as defibrillation of fibrillating hearts the pacing of arrested hearts and the like.

A problem which presents in the use of such independent electrodes, however, (particularly outside-of-hospitals), is that reliable, repeatable placement upon a subject's body is difficult. For instance, it is generally accepted that a majority of the errors encountered in acquiring ECG data, (particularly that to be archived for serial comparison), is caused by improper electrode placement by medical technical staff.

Of relatively recent development are flexible electrode pads which comprise a multiplicity of electrodes affixed thereto in an appropriate pattern for use in medical analysis and/or therapy. For instance, a Patent to Manoli, No. 4,583,549 describes an ECG electrode chest pad in which six (6) conductive discs are plated and etched on a flexible adhesive pad in a clinically conventional predetermined pattern effective for precordial 12 lead ECG electrode placement. Reproducible attachment of said six electrodes to a subject's chest in the proper arrangement for use with standard ECG machines is thus made possible by a single application of an electrode pad of an appropriate size for use with any particular subject. However, it would seem that the Manoli system would require a host of numerous sized electrode pads to accommodate subjects of different sizes as the Claims recite rather strict electrode placement criteria which are referenced with respect to a subject's body. A single electrode pad would not meet said requirements on subjects of different sizes. In addition, conductive discs made by plating and etching may not provide optimal electrodes for twelve lead ECG monitoring. A U.S. Pat. No. 4,121,575 to Mills et al. describes a multiple electrode device for application to a subject's chest, formed in stretchable non-conductive material having apertures in the V1–V6 positions. The capability for stretching the material is held to allow accurate positioning of V1–V6 electrodes on subjects of differing body size. It is noted that material under tension can lead to less than optimum subject fit and electrode operational characteristics in clinical settings. A Patent to Groeger et al., U.S. Pat. No. 4,957,109 describes an electrode assembly comprising right and left arm and leg leads, and precordial leads all affixed to a common structure. The arm and leg leads do not affix to a subject's chest during use. The Mills et al. and Groeger et al. systems do not serve to maintain a relatively fixed positioning of electrodes therein during use, and it is noted that movement between electrodes during use frequently causes confounding noise generation in electrocardiography systems. This is particulalry true where motion occurs between Limb Lead forming electrodes. Another U.S. Pat. No. 5,327,888 to Imran describes a precordial electrode strip which is supplied with detachable RA, LA and LL limb leads, which detachable limb leads are applied to subject limbs in use.

Patents to Way et al., U.S. Pat. Nos. 4,955,381 and 5,080,099 describe multiple conductive polymer pad containing electrodes for performing multiple electrical physiological functions from a set of electrodes with respect to a subject, at or about the same time, such as defibrillation, pacing and monitoring. Other Patents which disclose multiple electrode assemblies are U.S. Pat. No. 4,328,814 to Arkans and U.S. Pat. No. 5,191,886 to Paeth et al. These Patents each describe a plurality of electrodes configured in a physically seriesed configuration with conductive leads to various physically seriesed contacts, present at one end thereof. In addition, a Patent to Collins, U.S. Pat. No. 3,612,061 describes a porous sheet of elastic material which supports an array of electrodes adapted to contact a wearer's skin, and U.S. Pat. No. 5,184,620 to Cudahy et al. describes an electrode pad system comprised of a multiplicity of electrodes which are utilized in defibrillation and pacing scenarios as directed by an on-line computer driven analysis and electrical energy application system, which system distributes electrical energy to appropriate sets of said multiplicity electrodes in response to subject needs.

Continuing, it is to be understood that particularly appropriate materials in which to form an electrode pad with a plurality of ECG monitoring electrodes present therein are hydropolymers. This is because hydropolymers can be pliable, self-adhesive and compatible with maintaining the requisite hydration, (and consdquent mechanical and electrical stability), of subject skin to which they affix during prolonged use. The pliable property makes hydropolymers exceptionally well suited for application to unpredictable surface irregularities of various subject's chests and the self-adhesive property negates the need to apply non-aquous based or other potentially subject skin irritating adhesive material to affix the present invention to a subject's body during use. As well, the need to separately apply electrically conductive paste to electrically conducting areas of electrodes becomes unnecessary.

A U.S. Pat. No. 5,331,959 to Imran, describes a low impedance dry conforming contact member in which are present rods or filaments which are cured into material such as a silicon-based material, such that when configured as an electrode provide impedance reducing projections which protrude into the pores of a subject's skin during use. Said rods or filaments are held to reduce the need to use conductive paste. Another U.S. Pat. No. 4,524,087 to Engel, describes a conductive electrode application comprising an adhesive, swellable, dermally-nonirritating, conformable, ionic hydropolymer biomedical electrode fabricated by a claimed process.

Continuing, three Patents to Keusch et al, U.S. Pat. Nos. 4,706,680, 4,989,607 and 5,143,071 describe hydrogels which are caused to be highly conductive by the inclusion of an essentially uniformly distributed active electrolyte therein. Said Patents state that to form the hydrogels a polymeric mixture is caused to become cross-linked by exposure to radiant energy. This causes a gel-like solid to form which is sufficiently tacky and adhesive to adhere to subject's skin and which is substantially non-stringy and non-aggressive so that subject comfort is protected.

A Patent to Highe et al., U.S. Pat. No. 5,289,822 describes an electrode formed of a dry-conductive material having an outer surface for placement in contact with a subject's skin. A composition is deposited on at least a portion of the surface of the dry-electrode which comprises a plurality of water-containing vesicles. The purpose of said water-containing vesicles being to effect an immediate lowering of subject skin resistance upon the application of the electrode. It is stated that a period of approximately four minutes is otherwise required for moisture from a subject's skin to naturally occur at the electrode.

A Patent to Schmid, U.S. Pat. No. 5,124,107 describes a process for manufacturing a body electrode which comprises one or more galvanically active sensors which are combined with a first layer capable of adhering to a subject's skin, on a body contact side thereof. A second covering or supporting layer is also present on the opposite side of the body electrode. The process for manufacture provides that the two layers are sequentially cast in a mold which provides intended shape and size. The procedure avoids manufacturing problems encountered where electrodes are stamped from a preformed sheet. A potential problem of using such an electrode as provided by the Schmid 107 Patent is that it provides a laterally oriented conductive path between said galvanically active sensors through the first layer thereof. Electrically anisotropic conducting hydropolymers would be preferable.

Continuing, a Patent to Suyama et al, U.S. Pat. No. 5,132,058 describes a process for producing an anisotropically electroconductive sheet having a plurality of electroconductive portions extending in the direction of the thickness of the sheet. Application of an anisotropic magnetic field is utilized to draw electroconductive particles into a molding material such that said electroconductive particles gather where said electromagnetic field is applied. Another Patent which describes a similar system to that achieved by practice of the Suyama et al. Patent is U.S. Pat. No. 4,778,635 to Hechtman et al. A Patent to Kashiro et al., U.S. Pat. No. 4,209,481 describes an anisotropically electroconductive sheet in which electroconductive wires are formed into patterned groupings, which patterned groupings are in turn formed into patterns. The wires are parallel in the direction of the sheet thickness, and spaced apart by non-electroconductive elastomer. Another U.S. Pat. No. 5,045,249 to Jin et al., describes electrical interconnections made by means of a layer or sheet medium comprising chains of magnetically aligned, electrically conductive particles in a nonconducting medium. End particles of chains protrude from a surface of the medium to effect electrical contact. A Patent to Abraham et al. describes an electrode for use with electrosurgical apparatus which provides capacitive coupling with the skin of a subject. The electrode includes a conductive plate connected to the electrosurgical apparatus with an insulating layer disposed in contact with the conductive plate and on the opposite face of the insulator there is provided conductive material in the form of a plurality of discrete islands of conductive adhesive material which contact the skin of a subject during use. Another U.S. Pat. No. 5,232,639 to Reitz et al. describes a process for forming articles with anisotropic void distributions therein.

Of recent issue is a Patent to Kelly et al. U.S. Pat. No. 5,916,159, which describes an electro-dermal connector device with electrodes present therein for monitoring twelve lead ECG's. This Patent Claims spacing between precordial electordes V1–V2 to (2.0+/−0.56) inches, and spacing between precordial electrodes V2–V4 to (3.5+/−1.0) inches, but also teaches that relative spacing and positioning between V1, V2, V3 and V4 should remain constant in a family of electro-dermal connector devices, where the difference from member to member in said family is found in the spacing between V4–V5 and V5–V6, with demonstrative distances being 1.75, 2.5 and 3.5 inches. It is noted that it is not readily apparent why the Kelly et al. Patent selected the dimensions recited therein, as they do not seem to have any definite scientific basis and no data to show why, for instance positioning precordial leads V1 and V2 with respect to one another outside the range of (2.0+/−0.56) inches would result in unacceptable ECG monitoring. It is known by the present inventor, for instance, that, in adults, placing V2 three (3.0) inches from V1, (which is consistant with original published relative anatomic V1 and V2 positioning and still meets present standards), provides excellent ECG monitoring results, as does placing V2 less than one-and-forty-four hundreths (1.44) inches apart in pediatric subject. Another Patent to Kelly et al. is U.S. Pat. No. 6,006,125. This Patent teaches a "universal" ECG multiple sensor dermal chest mask with indicia thereon for aiding in application to a subject constituting means to align with a mid-sternum and the forth intercostal space, said mask having nine sensors thereon, which nine sensors are selected for application in specific cases to provide three sets of six sensors each, the essential condition being that there are present two sensors which can be selected at each of the V5 and V6 locations, with a third sensor being located thereinbetween which can be used as either a V5 or V6 sensor. The strict dimensions provided, (to the hundredths decimal place or more), it is believed, allow well defined criteria for designing therearound to avoid the Claims which recite restrictive dimensions, and regarding Claims wherein dimensions are not recited, avoidance is believed accomplished by varying the relative positions of V1, V2, V3 and V4 in a family of electro-dermal connector devices, in addition to varying distances between V4–V5 and V5–V6. In fact, scaling all electrode placements in members of a family of electrodes is thought to be preferable by the present inventor. As regards the presence of only two electrodes at V5 and at V6 locations, and the sharing of a third electrode by V5 and V6, it is unclear as to how lateral curents between said V5 and V6 electrodes are to be prevented especially where the electrode which can be a V5 or a V6 is utilized, and it is also unclear as to whether U.S. Pat. No. 5,184,620 to Cudahy et al. was considered in the examination of the 125 Patent Claiming said "universal" electrode.

Continuing, it is also established that electrode configuration can be important in determining the accuracy of monitored signals. For instance, the use of a Bulls-eye shaped electrode, which comprises a central electrode surrounded by one or more annular ring electrodes, can provide signals which focus upon a specific region of a subject's heart, which focus is not available when a simple electrode geometry is utilized. As well, Bulls-eye shaped electrodes allow determination of derivatives of detected signals in use.

An article by He et al. titled "Body Surface Laplacian Mapping of Cardiac Electrical Activity" published in The American J. of Cardiology, Vol. 70, Dec. 15, 1992 describes the use of Bulls-eye shaped electrodes to map derivatives of cardiogenic signals.

Patents which describe unusual geometrical electrode configurations are, for instance, a Patent to Clare et al., U.S. Pat. No. 5,295,482 which discloses a large surface area electrode in which a central portion is surrounded by two surrounding ring portions., said central and two surrounding ring portions being separated from one another by annular regions. This Patent states that during use in theraputic applications, current density is found to be greater at the outer edge of an electrode than it is at a more central location. The purpose of the described system is disclosed as being to effect a more uniform distribution of current density over the effective large surface area of the disclosed electrode during use, by providing multiple "outer-edge" providing portions. Other references which describe the "edge-effect" are a Patent to Dahl et al., U.S. Pat. No. 5,063,932 and a Canadian Patent No. 1,219,642. In addition, two articles also treat the subject, said articles being: "Optimal Electrode Designs for Electrosurgery, Defibrillation, and External Cardiac Pacing", by Kim et al., which appeared in Transactions On Biomedical Engineering, Vol. BME-33, No. 9, September 1986; and "Analysis and Control of the Dispersive Current Distribution under Circular Dispersive Electrodes", by Wiley and Webster, which appeared in the IEEE Transactions On Biomedical Engineering, Vol. BME-29, No. 5, in May 1982.

Even in view of the above cited literature, need remains for a convenient to utilize bioelectric interface, which bioelectric interface comprises equivalent Einthoven triangle limb electrodes mounted on a common subject chest applied support sheet, which preferably comprises an electrically anisotropic conducting hydropolymer self adhesive material, which provides electrodes of a composition and geometry appropriate for optimizing electrical contact to a subject, which allows clinically accurately monitored signals to be obtained therefrom during use, and which facilitates a multiplicity of non-monitoring uses such as external cardiac pacing, cardiac defibrillation, electro surgery, electro-ablation processes, and impedance cardiography.

DISCLOSURE OF THE INVENTION

As described in Co-pending application Ser. No. 08/374, 873 filed Aug. 16, 1999, the present invention concerns the practice of electrocardiology wherein a number of signals, which are diagnostic of myocardial function, are acquired via sensors placed upon a subject's body. The present invention differs from previous teachings in that a BIO-ELECTIC INTERFACE ADAPTER WITH TWELVE-LEAD ECG CAPABILITY AND PROVISION FOR DEFIBRILLATION AND/OR PACING is described. In particular, the system of the present invention Bio-electric interface, as regards twelve-lead monitoring capability, remains as previously described in the 873 Application, and disclosure from that Application is incorporated by reference herein, and largly repeated hereafter for emphasis. What is new, novel and non-obvious in this Application, however, is the design of the Bio-electric interface to include not only twelve-lead monitoring capability, but also to includes, amongst other things, provision of standard defibrillation electrodes. This takes at least two forms:

First, the outer edge of the 873 Bio-electric interface can be of an undulated shape, as previously taught in the 873 Application, but undulated appropriately to allow convenient placement of two separate element large-area defibrillation and/or pacing electrodes on a subject simultaneous therewith, (eg. near locations where prior embodiments had placed right-arm and left-leg electrodes and because of their similar size, near conventional locations thereof), and Second, large-area defibrillation electrodes can be integrally combined as a Bio-electric interface, and in most cases serve as right-arm and/or left-leg electrodes when not being utilized as defibrilltion electrodes, or said large-area defibrillation electrodes can have smaller monitoring limb lead forming electrodes integrally attached thereto or otherwise included therewith. Of course, the presence of perforations, or other functionally equivalent means, to allow easy detachment and deployment of the large-area defibrillation electrodes can be a feature, as can presence of perforations or other functionally equivalent means to allow detachment and deployment of said right-arm and left-leg electrodes from the new Bio-electric interface configuration, for other diagnostic or theraputic purposes.

A present invention bioelectric interface preferably comprises sufficient precordial electrodes to monitor standard twelve lead ECG's along with said defibrillation electrodes as an integral part thereof. The defibrillation electrodes can be affixed via perforations or functional equivalent, so as to allow easy detachment thereof. The defibrillation electrodes can have affixed thereto electrodes appropriate for use in forming right-arm and left-leg limb leads. The present invention Bioelectric interface can comprise limb lead forming electrodes (RA) (LA) and (LL), and the present invention Bioelectric interface can further comprise a harness thereon to which is affixed, in use, a bundle of wires or tracks for connecting the interface to compatable diagnostic and theraputic systems.

The present invention can be recited as a bioelectric interface comprising at least two defibrillation electrodes as an integral part thereof, said bioelectric interface further comprising sufficient precordial electrodes to monitor standard twelve lead ECG's. The bioelectric interface can provide the defibrillation electrodes affixed to the bioelectric interface via perforations or functional equivalent, so as to allow easy detachment thereof, and the defibrillation electrodes can have affixed thereto electrodes appropriate for use in forming right-arm and left-leg limb leads. The present invention bioelectric interface preferably further comprises ECG limb electrodes (RA) (LA) and (LL) configured in an RA, LA, LL electrocardiogram system electrode pattern; which RA, LA and LL electrodes, when functionally combined with summing impedances from each thereof, which summing impedances are "Y" interconnected to provide a Wilson central terminal, form an Einthoven frontal lead triangle with a I, II, III lead pattern when mounted to a subject's chest, said Einthoven frontal lead triangle with a I, II, III lead pattern being positioned on said subject's chest so as to provide a voltage which presents at said Wilson central terminal which is within a selected range of deviation from a voltage which would appear at a Wilson central terminal formed from summing impedances from conventional limb mounted electrodes which are "Y" interconnected, (both voltages being with resepct to some reference). In addition, the present invention bioelectric interface can further comprise at least one selection from the group consisting of:

said bioelectic interface comprises a harness thereon to which is affixed, in use, a bundle of wires or tracks for connecting to diagnsotic and/or theraputic systems;

said at least two defibrillation electrodes are connected to a source of defibrillation electrical energy;

said precordial electrodes are connected to a system for monitoring twelve lead ECG's.

six precordial and three limb lead electrodes are located as:

electrode region RA generally in the region of the first or second intercostal space to the right of the sternum;

electrode region LA generally in the region of the left third or fourth intercostal space at the mid-axillary line;

electrode region LL generally in the region of the inferior costal margin in the left mid-clavicular line;

electrode region V1 in the region of the fourth intercostal space at the right sternal border;

electrode region V2 in the region of the fourth intercostal space at the left sternal border;

electrode region V4 in the region of the fifth intercostal space at the left mid-clavicular line;

electrode region V3 in the region of the midpoint between electrode regions V2 and V4;

electrode region V5 in the region of the fifth intercostal space in the left anterior axillary line; and electrode region V6 in the region of the fifth intercostal space in the mid-axillary line.

Another recitation of a present invention bioelectric interface provides that it comprise a carrier matrix in functional combination with at least two spatially separated defibrillation electrodes, and V1, V2, V3, V4, V5, and V6 precordial electrodes and RA, LA and LL limb lead forming electrodes, said electrodes being affixed to said carrier matrix in a manner such that their relative positions with respect to one another are essentially fixed, said RA, LA, LL limb lead electrodes being positioned such that when functionally combined with summing impedances from each thereof, which summing impedances are "Y" interconnected to provide a Wilson central terminal, form an Einthoven frontal lead triangle with a I, II, III lead pattern when mounted to a subject's chest, said Einthoven frontal lead triangle with a I, II, III lead pattern being positioned on said subject's chest so as to provide a voltage which presents at said Wilson central terminal which is within some selected range of deviation from a voltage which would appear at a Wilson central terminal formed from summing impedances from conventional limb mounted electrodes which are "Y" interconnected. Said bioelectric interface preferably further comprises an adhesive comprised of electrically conductive polymer which is hydrophillic, and thereby particularly well suited for application to human skin. Further, said electrodes are each of a construction such that contact with the adhesive sheet is essentially continuous over the dimension of each said electrode, and at least one of said electrodes can be of a multiple-piece construction such that each of said multiple pieces contacts the adhesive independently and essentially continuously over the dimension of each said multiple pieces, (eg. multipiece construction configures a Bulls-eye pattern). It is further noted that the adhesive sheet can be affixed so as to sandwich said electrodes between said carrier matrix and said adhesive sheet, the purpose being to improve subject adherence. Also, said bioelectric interface can further comprise means for electrically connecting said electrodes to external devices. It is further noted that the adhesive sheet preferably simultaneously presents with essentially anisotropic specific, (ie. bulk), impedance properties and essentially isotropic pliability and adhesion mechanical properties, electrode(s) in each of said spatially separated regions of electrode(s) being affixed to said adhesive sheet in a manner such the relative positions of electrodes present with respect to one another are essentially fixed, and such that the specific impedance from each electrode in said regions of spatially separated electrode(s) directly through the thickness of said adhesive sheet, is less than that between any two electrodes in different spatially separated regions of electrodes) through said adhesive sheet, said electrical anisotropic specific impedance properties of said adhesive sheet being the result of at least one selection from the group consisting of:

scrim therein, which scrim is a web of disimilar materials, (or a material with regionally altered characteristics), with relatively electrically conductive adhesive material present in open areas of said web so as to form channel regions of electrically conductive adhesive material bordered by said scrim material, such that adhesive material in one channel region does not contact that in other regions; and slits therein, which slits are positioned between electrodes.

A method of defibrillating a subject comprising the steps of:

a. providing a bioelectric interface as described; and b. affixing said bioelectric interface to a subject and causing the defibrillation electrodes therein to be electrically attached to a defibrillation system and applying a defibrilating shock therewith through said defibrillation electrodes.

Said method can further comprise performing a procedure selected from the group consisting of;

a. cardio-pulmonary resuscitation b. ECG monitoring;

c. cardiac pacing;

d. electro surgery;

e. electro-ablation;

f. impedance cardiography;

g. transdermal drug or nutrient transfer; and h. electromechanical energy transfer or detection on said subject without removing said bioelectric interface.

A present invention bioelectric interface can be characterized by at least one selection from the group consisting of:

a. an adhesive sheet is affixed to said support sheet on a subject contacting side thereof and simultaneously presents with essentially anisotropic electrical impedance properties and essentially isotropic mechanical pliability and adhesion properties, said electrodes being affixed to said adhesive sheet such that the impedance from each said electrode directly through the thickness of said adhesive sheet, is less than that between any two of said electrodes through said adhesive sheet;

b. perforations are present in said support sheet which allow easy detachment and deployment of at least one of said Einthoven frontal lead triangle RA, LA and LL electrodes, so that said at least one of said Einthoven triangle RA, LA, and LL electrodes is/are, in use, positionable at locations selected from the group consisting of:

in contact with a subject's chest; and in conventional Einthoven triangle forming subject limb positions;

c. perforations are present in said support sheet which allow easy detachment and deployment of at least one of said defibrillation electrodes;

d. an undulated outer edge on said bioelectric interface support sheet; and e. at least one hole through said bioelectric interface support sheet which allows access to the skin of a subject to which it is affixed in use, (note, support sheet material retained from the hole can serve to form an attached "flap", to which, for instance, a wire harness can be secured in use).

f. at least one said electrocardiogram system electrode which comprises spring-loaded means on a non-subject contacting side thereof, which spring-loaded means develops compression derived force when caused to be compressed, the purpose thereof being to facilitate electrical contact to an electrically conductive element caused to be placed in contact therewith in use, by development of said compression derived force.

Another recitation of a present invention embodiment provides that it be a combination of two defibrillation electrodes and a bioelectric interface which comprises a support sheet in which are affixed sufficient precordial and limb lead forming electrodes to enable standard twelve lead ECG monitoring, said bioelectric interface having an undulated outer edge. The support sheet can have at least one hole, (and optionally a "flap"), therein for use in aligning with subject anatomy, (over for instance the Sternum). Further, the undulations in the support sheet and the shape of the defibrillation electrodes are such as to closely mate. Where a flap is present it can serve as a force absorbing support for attaching a cable bundle to the bioelectric interface.

(Note, as discussed in the Detailed Disclosure Section of this Specification, FIGS. 8b and 10a–10e provide insight to exemplary present invention Bio-electric interface embodiements which include two defibrillation electrodes, as well as sufficient precordial and limb lead forming electrodes to enable standard twelve-lead monitoring capability).

Continuing, for general insight and as disclosed in prior Applications from which this Application continues, it is to be appreciated that the practice of electrocardiography involves subject contacting electrodes spatially oriented in lead configurations such as Einthoven triangle, Frank, McFee, Schmidt, twelve-lead configurations etc., and in array patterns for use in mapping, etc., and the present invention bioelectric interface continues as a system which provides Right-Arm (RA), Left-Arm (LA) and Left-Leg (LL) electrodes which form, when applied to a subject's chest in use, an Einthoven frontal lead triangle with an equivalent I, II, III lead pattern, said pattern being determined as acceptable by presentation of a voltage with respect to a reference at a formed Wilson central terminal, which voltage with respect to a reference is within a selected range of deviation from a voltage with respect to a reference presented at a conventionally formed Wilson central terminal using conventional subject limb positioning of RA, LA and LL electrodes. The present invention bioelectric interface further provides all necessary electrodes, appropriately configured for mounting to a subject's chest, for use with electrocardiograph systems, and in the most recent embodiment provides provision for simultaneous presence of defibrillation electrodes, either as separate elements, or as an integral part of the Bio-electric interface.

As demonstrated in the Background Section of this Disclosure, multiple electrode systems are not unknown. However, said known systems do not provide all electrodes for use with a twelve-lead electrocardiogram (ECG) system conveniently positioned on a bioelectric interface which can be easily, accurately and repeatably applied to a subject's chest in a desired anatomical orientation. A twelve-lead (ECG) system, by conventional practice, requires that electrodes be placed on a subject's Right (RA) and Left (LA) arms and Left leg (LL), and that six precordial electrodes (V1, V2, V3, V4, V5, and V6), be placed upon the subject's chest. The locations of the V1–V6 electrodes are:

V1—in the region of the fourth intercostal space at the right sternal border;

V2—in the region of fourth intercostal space at the left sternal border;

V4—in the region of fifth intercostal space at the left mid-clavicular line;

V3—in the region of the midpoint between the V2 and V4 electrodes;

V5—in the region of the fifth intercostal space at the left anterior axillary line;

V6—in the region of the fifth intercostal space in the left mid-axillary line.

No known reference, however, suggests that arm and leg equivalent electrodes should be placed at chest locations relatively near the precordial electrodes. The present invention teaches that said arm and leg equivalent electrodes are to be so placed. The location of said arm and leg equivalent electrodes is best understood by reference to the Drawings which are discussed in the Detailed Description of this Disclosure, however, verbally their positioning can be generally described as, in a non-limiting manner, as:

Right Arm—generally in the region of the first or second intercostal space to the right of the sternum;

Left Arm—generally in the region of left thrid or fourth intercostal space at the mid-axillary line; and Left Leg—generally in the region of the inferior costal margin in the left mid-clavicular line.

It is emphasized that where limb lead forming electrode placement is the topic, it is the functional achievement of a Wilson Central Terminal voltage to which precordial lead electrode signals can be compared which is important, rather than precise subject referenced anatomical positioning of electrodes.

In addition, the present invention teaches the optional use of multiple electrode element electrodes, (eg. "Bulls-eye" shaped electrodes), for instance, in a multiple electrode element electrode system. Use of single electrode element "Button" electrodes is conventional, and in use each such Button electrode serves to measure an electrical signal between it and a common or reference electrode, (typically termed uni-polar electrodes), or a similar button electrode (typically termed Bi-polar electrodes). When multiple electrode element (eg. Bulls-eye), electrodes are utilized, however, signals are generated between two components of a single electrode. Continuing, a Bulls-eye shaped electrode is typically configured like a "target". That is, typically a Button electrode will be centrally located within an outer annular shaped electrode. The benefits provided by such multi-electrode element electrodes are the ability to achieve greater resolution of signals generated in a specific area of a subject's heart, and it is noted, that the signals measured are representative of the derivatives of electrical signal activity produced by a subject's heart. That is, the signal provided between a Button and First Annulus is proportional to a derivative of a signal generated by a subject's heart. Additional annular ring electrodes can also be present and signals measured thereby are proportional to higher order derivatives. Use of Bulls-eye" electrode geometry then allows investigation of High Frequency aspects of electrical activity generated by a subject's heart. It is noted that a limitation is associated with the use of Bulls-eye electrodes in that the smaller they are dimensioned, although enabling increased resolution and investigation of electrical signals generated in smaller regions in a heart, the smaller the magnitude of signal they provide. In a multiple electrode setting then, where relative motion between electrodes can create confounding electrical noise, it then becomes increasingly important to prevent relative motion between electrodes and components of Bulls-eye electrodes, when Bulls-eye electrodes are present. (Note, it is emphasized that it is possible to achieve a result similar to that provided by "Bulls-eye" electrodes with other multiple element electrodes, and for the purposes of this Disclosure any functionally similar electrode is to be considered as included by the terminology "Bulls-eye" whether a closed annulus is present or not).

It is also to be understood that a present invention electrode can consist of a plurality of electrode elements, (eg. a plurality of button shaped electrode elements), configured in a region of the bioelectric interface which, in use, aligns with an anatomical location appropriate for use in a standard twelve-lead (ECG) system.

With the forgoing in mind, it is then to be appreciated that the system of the present invention is a bioelectric interface comprised of a plurality of electrodes which are affixed to a support sheet in a desired spatially separated pattern, such that in use said electrodes are essentially fixed in location with respect to one another. It is noted that fixing said relative position between electrodes, and between electrode elements, serves to reduce electrical noise which can be generated when, in use, electrodes move with respect to one another. Again, it is to be understood that the electrodes can be of single electrode element, or multiple electrode element Button or Bulls-eye, (or other), geometry.

Continuing, a typical present invention bioelectric interface has an adhesive material present over at least a portion of a surface thereof which contacts a subject in use. The adhesive material of the present invention can have the properties of simultaneously demonstrating essentially electrically anisotropicity, but isotropic mechanical (eg. pliability and adhesion), properties. That is, the specific, (or bulk), impedance across the adhesive material can be significantly different from that laterally directed, but the mechanical properties such as adhesion and pliability are typically essentially consistent. (Note, the term "specific impedance" is used to refer to the regional bulk property of the adhesive material, rather than properties resulting from dimensions of sheets fabricated therefrom). In the preferred embodiment, the adhesive material is a hydropolymer sheet which demonstrates a tackiness on a subject skin contact side thereof. Hydropolymers are particularly applicable in realization of the present invention as they are electrically conductive, relatively nonirritating to a subject's skin, and they demonstrate excellent adhesive qualities. Commercially available hydropolymer sheets with isotropic electrical properties, are available under the Tradename "Promeon" from the Ludlow Group of Springfield Mass., under the product designation of RG-60 Series Hydrogels. Lec-Tec of Minneapolis, Minn. also markets hydrogels. The present invention provides that such adhesive hydropolymer sheet material can be utilized, if "slits" are entered thereto at appropriate locations to effect electrical anisotropicity between electrodes present at various laterally offset locations. It is noted that hydropolymer sheets do not typically demonstrate a rigidity sufficient to maintain a spatially stable relationship between electrodes affixed thereto, but particularly when slits are formed therein, hence, the present invention requires that a support sheet carrier matrix be present to which electrodes and said adhesive sheet attach. That is, the system of the present invention will then comprise a support sheet carrier matrix to which are attached, at desired spatially offset locations, electrodes, over which configuration said hydropolymer is placed so that said electrodes are sandwiched between said carrier matrix and hydropolymer. At locations between the various electrodes said "slits" are then caused to be present by, typically, a mechanical process. It is noted that in practice said slits need not be of a degree to provide complete discontinuity between various regions of the resulting hydropolymer system to provide a sufficiently anisotropic specific impedance system. The Background Section also identifies various electrically anisotropic adhesive materials. The present invention, in addition, teaches that an essentially electrically anisotropic adhesive material sheet can be provided by a "Scrim" material comprising a number of channels therethrough, which channels are caused to be filled with an electrically conductive adhesive material, (preferably a hydropolymer), such that "island channels" of conductive material exist across the resultant sheet, but such that electrically nonconductive scrim exists between laterally oriented islands of conductive material. The "Scrim" can be electrically conductive carbon fibers, and/or electrically non-conducting plastic filaments, or materials which have been regionally altered to vary conductivity from one region to another, as required to provide a desired electrical anisotropicity.

It is also noted that as the relative spatial separation of various electrodes is essentially fixed by the present invention, and as their position on a subject's body is typically secured by an adhesive sheet, it is possible to conduct activities such as cardio-pulmonary-resuscitation (CPR) on a subject to which the present invention bioelectric interface is applied, without removal thereof. Such is essentially impossible where individual leads are utilized in an (ECG) system. As well, the present invention teaches that the means for making electrical contact to the electrodes should be available on the outer, non-subject contact, surface of the bioelectrical interface. For instance, snaps might be provided so that leads from any (ECG) system can easily attach thereto, or so that conductive tracks can be employed to bring signals to a manifold or connector means for convenient electrical access.

It is also emphasized that the electrodes in the bioelectric interface, being electrically conductive, enable, in an emergency, the application of defibrillation via "metal-paddle-type" electrodes to said interface means for making intimate electrical contact to said electrodes without removing the present invention bioelectrical interface from the subject. And, because the present invention is firmly affixed to a subject, the defibrillation shock will be safely transmitted to the subject with little, or no attenuation. It is also emphasized that in use, first and second conventional paddles of a defibrillation system can be caused to contact first and second spatially separated groups of electrodes in the bioelectric interface, press contacted electrodes into good electrical contact with the subject, and deliver electrical defibrillating pulse energy therethrough. Further, the presence of multiple electrodes, (and even multiple electrode elements within an electrode), within a defibrillation paddle-sized cluster of electrodes, through which defibrillation electrical energy can be delivered to a subject, serve to reduce adverse edge effects associated with applying defibrillation electrical energy through single element paddle, (or pad), electrodes. Special electrodes can be specifically designed which serve to reduce edge effects, and use thereof in the present invention Bio-electric interface is within the scope of the present invention.

One can also utilize one or more electrodes in the present invention bioelectric interface for heart pacing, electrosurgery, electro ablation, impedance cardiography, transdermal drug or nutrient transfer and electromechanical energy transfer.

The present invention bioelectric interface can be better described, in its most basic form, as comprising a support sheet in functional combination with at least three (3) spatially separated electrocardiogram system electrodes, with each of said at least three (3) spatially separated electrocardiogram system electrodes being a single electrical electrode element or a group of electrically independent electrode elements. Each of said spatially separated electrocardiogram system electrodes is affixed to said support sheet in a manner such that the relative positions of said electrocardiogram system electrodes with respect to one another are essentially fixed therewithin. Three (3) of said at least three (3) electrocardiogram system electrodes being configured in an RA, LA, LL electrocardiogram system electrode pattern. The positioning of said three (3) electrocardiogram system electrodes as applied to a subject's chest during use can, in a non-limiting manner, be exemplified as follows:

electrode RA being generally in the region of the first or second intercostal space to the right of the sternum;

electrode LA being generally in the region of the left third of fourth intercostal space in the mid-axillary line;

electrode LL being generally in the region of the inferior costal margin in the left mid-clavicular line;

Further, said electrodes RA, LA and LL form, when applied to a subject's body in use, an Einthoven frontal lead triangle with an equivalent I, II, III lead pattern which is determined as acceptable by presentation of a voltage with respect to a reference at a formed Wilson central terminal, which voltage with respect to a reference is within a selected range of deviation from a voltage with respect to a reference presented at a conventionally formed Wilson central terminal using conventional subject limb positioning of RA, LA and LL electrodes. Said user selected range of voltage deviation can be selected to be less than one (1.0) millivolt, one (1.0) millivolt, or greater than one (1.0) millivolt.

The present invention bioelectric interface can further comprise an equivalent electrocardiogram system RL electrode, and said RA, LA, LL and RL electrodes can be present in the support sheet such that perforations allow easy detachment of said equivalent electrocardiogram RA, LA, LL and RL electrodes, in use, thereby allowing them to be automatically positioned at a location in contact with a subject's chest, or by manual manipulation, in conventional subject limb positions.

The present invention bioelectric interface support sheet is typically at least partially covered with an adhesive material on a subject contacting side thereof, and said adhesive material can present with electrical conductive properties which can be isotropic, or regionally anisotropic such that the specific impedance through said adhesive material in certian areas is less than that in a laterally oriented direction. Said regional anisotropic electrical conductive properties of said adhesive material can be effected, as described infra herein, by the presence of an electrically conductive and/or nonconductive scrim patterned therein so as to form channel regions of electrically conductive adhesive material through said adhesive material bordered by said scrim material, such that adhesive material in one channel region does not contact that in other regions. An alternative approach to effecting said regional anisotropic electrical conductive properties of the adhesive material involves the placing of slits therein. Said adhesive material can be a hydropolymer and it can be caused to cover essentially the entire subject contacting surface of said support sheet.

As mentioned, at least one of said spatially separated electrocardiogram system electrodes can be of a construction consisting of a group of electrically independent electrode elements, and said elements can be configured in, for instance, Bulls-eye and multiple button shaped electrode elements patterns.

A method of providing an Einthoven triangle equivalent RA, LA, LL pattern of electrodes on the chest of a subject, utilizing the present invention bioelectric interface, can comprise the steps of:

a. Providing a present invention bioelectric interface comprising a support sheet in functional combination with at least three (3) spatially separated electrocardiogram system electrodes as already described, wherein at least one (1) of said at least three (3) spatially separated electrocardiogram system electrodes is of a construction consisting of a group of electrically independent electrode elements. As described above, each of said spatially separated electrocardiogram system electrodes is affixed to said support sheet in a manner such the relative positions of said electrocardiogram system electrodes with respect to one another are essentially fixed therewithin. Three (3) of said at least three (3) electrocardiogram system electrodes are configured in an RA, LA, LL electrocardiogram system electrode pattern, such that said three (3) electrocardiogram system electrodes can be applied on a subject's chest during use as follows:

electrode RA being generally in the region of the first or second intercostal space to the right of the sternum;

electrode LA being generally in the region of the left third or fourth intercostal space in the mid-axillary line;

electrode LL being generally in the region of the inferior costal margin in the left mid-clavicular line;

Also as described above, said electrodes RA, LA and LL form, when applied to a subject's body in use, an Einthoven frontal lead triangle with an equivalent I, II, III lead pattern which is determined as acceptable by presentation of a voltage with respect to a reference at a formed Wilson central terminal, which voltage with respect to a reference is within a selected range of deviation from a voltage with respect to a reference presented at a conventionally formed Wilson central terminal using conventional subject limb positioning of RA, LA and LL electrodes. Said user selected range of voltage deviation can be selected to be less than one (1.0) millivolt, one (1.0) millivolt, or greater than one (1.0) millivolt;

b. Applying said bioelectric interface to a subject;

c. Selecting at least one electrically independent element in each of said at least one electrocardiogram system RA, LA and LL electrode(s) consisting of a group of electrically independent electrode elements;

d. Connecting said selected electrocardiogram system electrically independent element(s) in each of said RA, LA and LL electrode(s) to appropriate inputs of an electrocardiogram system.

Continuing, a preferred embodiment of the present invention bioelectric interface comprises a support sheet in functional combination with at least nine (9) spatially separated electrocardiogram system electrodes. Each of said at least nine (9) spatially separated electrocardiogram system electrodes being a single electrical electrode element or a group of electrically independent electrode elements. Each of said spatially separated electrocardiogram system electrodes is affixed to said support sheet in a manner such the relative positions of said electrocardiogram system electrodes with respect to one another are essentially fixed therewithin, with nine (9) of said at least nine (9) electrocardiogram system electrodes being configured in an RA, LA, LL, V1, V2, V3, V4, V5, V6 electrocardiogram system electrode pattern. In use, said nine (9) electrocardiogram system electrodes can be applied to a subject's chest during use as follows:

electrode RA being generally in the region of the first or second intercostal space to the right of the sternum;

electrode LA being generally in the region of the left third or fourth intercostal space in the mid-axillary line;

electrode LL being generally in the region of the inferior costal margin in the left mid-clavicular line;

Said electrodes RA, LA and LL form, as described infra herein, when applied to a subject's body in use, an Einthoven frontal lead triangle with an equivalent I, II, III lead pattern which is determined as acceptable by presentation of a voltage with respect to a reference at a formed Wilson central terminal, which voltage with respect to a reference is within a selected range of deviation from a voltage with respect to a reference presented at a conventionally formed Wilson central terminal using conventional subject limb positioning of RA, LA and LL electrodes. Said user selected range of voltage deviation can be selected to be less than one (1.0) millivolt, one (1.0) millivolt, or greater than one (1.0) millivolt.

The V1, V2, V3, V4, V5, V6 electrocardiogram system precordial electrode pattern is formed as:

electrode V1 in the region of the fourth intercostal space at the right sternal border;

electrode V2 in the region of the fourth intercostal space at the left sternal border;

electrode V4 in the region of the fifth intercostal space at the left mid-clavicular line;

electrode V3 in the region of the midpoint between electrode groups V2 and V4;

electrode V5 in the region of the fifth intercostal space in the left anterior axillary line; and electrode V6 in the region of the fifth intercostal space in the left mid-axillary line.

The described preferred embodiment of the present invention can also further comprise an equivalent electrocardiogram system RL electrode, and perforations can be present in said support sheet to allow easy detachment and deployment of said equivalent electrocardiogram RA, LA, LL and RL electrodes, in use, so that they can be positioned in contact with a subject's chest, or in conventional subject limb position.

As described above, the presently described present invention bioelectric interface support sheet is also typically at least partially covered with an adhesive material on a subject contacting side thereof, which adhesive material presents with electrical conductive properties which can be isotropic or regionally anisotropic such that the specific impedance through said adhesive material is less than that in a laterally oriented direction. As also already discussed, a preferred adhesive material is hydropolymer which covers essentially the entire subject contacting surface of said support sheet.

Also as discussed above, each of the electrodes can be of a construction consisting of a group of electrically independent electrode elements, such as a Bulls-eye pattern, and multiple button shaped electrode elements.

A method of defibrilating a subject can comprise the steps of:

a. Providing a bioelectric interface comprising a support sheet in functional combination with at least two (2) spatially separated defibrillation electrodes, as just described;

b. Affixing said bioelectric interface to a subject as described above, and causing electrodes therein to be electrically attached to a defibrillation system and delivering a defibrillation shock.

Said method of acquiring electrocardiographic data said method of acquiring electrocardiographic data can further include the step of removing and deploying said electrodes RA, LA and LL configured in an Einthoven frontal triangle equivalent LA, RA, LL pattern, utilizing perforations in said support sheet, and affixing said RA, LA and LL electrodes to conventional subject limb locations.

A method of utilizing any present invention bioelectric interface during formation of an Einthoven triangle equivalent or during acquisition of electrocardiographic data, can further comprise the simultaneous step of performing a procedure selected from the group consisting of;

a. cardio-pulmonary resuscitation b. ECG monitoring;

c. cardiac pacing;

d. electro surgery;

e. electro-ablation;

f. impedance cardiography;

g. transdermal drug or nutrient transfer; and h. electromechanical energy transfer or detection;

on said subject without removing said bioelectric interface.

Where defibrillation is performed, two conventional defibrillation paddles are positioned so that a first conventional defibrillation paddle contacts at least two of said electrocardiogram system electrodes, and a second said conventional defibrillation paddles contacts at least two of said electrocardiogram system electrodes, said two at least electrodes contacted by said first conventional defibrillation paddle being different than, and spatially separated from, said at least two electrodes contacted by said second conventional defibrillation paddle. In use, electrodes contacted by defibrillation paddles are caused to be pressed firmly into good contact with a subject. The result of the presence of multiple electrodes being that defibrillation pulse current distribution electrode edge effects are reduced.

It is further noted that the voltage present at a formed Wilson central terminal can be a root-mean-square value of a selected portion of a subject electrocardiogram system monitored electrocardiogram cycle, such as the QRS complex.

Finally, it is noted that a conventional Wilson central terminal is a central "Y" interconnection point of fixed value, (eg. 10,000 ohm), resistors attached to RA, LA and LL electrodes. The present invention provides that at least one of said resistors can be variable and can, in use, be adjusted and thereby set a Wilson central terminal voltage produced by use of a present invention Bioelectric Interface, to a desired value. The application of variable resistors in forming a Wilson central terminal in combination with a present invention Bioelectric Interface, to effect production of a Wilson central terminal voltage which is within a desired deviation value with respect to a similar voltage which would be obtained utilizing conventional limb positioned electrodes, is not, to the inventor's knowledge, obviated in any known rerference or combination of references.

The present invention will be better understood by reference to the Detailed Description Section in conjunction with the accompanying Drawings.

SUMMARY OF THE INVENTION

It is a primary purpose of the present invention to teach a bio-electric interface for application to a subject's chest during use, should be comprised of electrodes for monitoring ECG data, as well as providing for simultaneous presence of electrodes for applying defibrillation shocks, either as separate elements or integrated into said a bio-electric interface.

It is another primary purpose of the present invention to teach that electrodes configured in an RA, LA, LL electrocardiogram system electrode pattern in a bio-electric interface should be applied to a subject's chest during use, the positioning of said electrocardiogram system electrodes being exemplified as:

electrode RA being generally in the region of the first or second intercostal space to the right of the sternum;

electrode LA being generally in the region of the left third or fourth intercostal space at the mid-axillary line;

electrode LL being generally in the region of the inferior costal margin in the left mid-clavicular line;

said electrodes RA, LA and LL forming an Einthoven frontal lead triangle with an equivalent I, II, III lead pattern which is determined as acceptable by presentation of a voltage with respect to a reference at a formed Wilson central terminal, which voltage with respect to a reference is within a selected range of deviation from a voltage with respect to a reference presented at a conventionally formed Wilson central terminal using conventional subject limb positioning of RA, LA and LL electrodes. (Said user selected range of voltage deviation can be selected to be less than one (1.0) millivolt, one (1.0) millivolt, or greater than one (1.0) millivolt).

It is another primary purpose of the present invention to teach that electrodes configured in an RA, LA, LL electrocardiogram system electrode pattern in a bio-electric interface should be applied to a subject's chest during use, the positioning of said electrocardiogram system electrodes being such that said electrodes RA, LA and LL form an Einthoven frontal lead triangle with an equivalent I, II, III lead pattern which is determined as acceptable by presentation of a voltage with respect to a reference at a formed Wilson central terminal, which voltage with respect to a reference is within a selected range of deviation from a voltage with respect to a reference presented at a conventionally formed Wilson central terminal using conventional subject limb positioning of RA, LA and LL electrodes. (Said user selected range of voltage deviation can be selected to be less than one (1.0) millivolt, one (1.0) millivolt, or greater than one (1.0) millivolt).

It is another purpose of the present invention to teach that six precordial electrodes (V1, V2, V3, V4, V5, and V6) in said bioelectric interface, should also be placed upon the subject's chest in combination with said RA, LA and LL electrodes. The locations of the V1–V6 electrodes being exemplified as:

V1—in the region of the fourth intercostal space at the right sternal border;

V2—in the region of fourth intercostal space at the left sternal border;

V4—in the region of fifth intercostal space at the left mid-clavicular line;

V3—in the region of the midpoint between the V2 and V4 electrodes;

V5—in the region of the fifth intercostal space at the left anterior axillary line;

V6—in the region of the fifth intercostal space in the left mid-axillary line.

It is yet another purpose of the present invention to teach the use of multiple electrode element electrodes, (eg. "Bullseye" shaped electrodes), as well as single electrode element "Button" electrodes in a bioelectric interface.

It is still yet another purpose of the present invention to teach a bioelectric interface which has an adhesive material present over at least a portion of a surface thereof which contacts a subject in use.

It is yet still another purpose of the present invention to teach a bioelectric interface in which the adhesive material is a hydropolymer.

It is another purpose of the present invention to teach a bioelectric interface in which the adhesive material demonstrates anisotropic specific impedance.

It is yet another purpose of the present invention to teach a method of utilizing any present invention bioelectric interface during formation of an Einthoven triangle equivalent or during acquisition of electrocardiographic data, which further comprises the simultaneous step of performing a procedure selected from the group consisting of;

a. cardio-pulmonary resuscitation b. ECG monitoring;

c. cardiac pacing;

d. electro surgery;

e. electro-ablation;

f. impedance cardiography;

g. transdermal drug or nutrient transfer; and h. electromechanical energy transfer or detection;

on said subject without removing said bioelectric interface.

It is still yet another purpose of the present invention to teach a bioelectric interface comprised of a plurality of electrodes which are affixed to a support sheet in a desired spatially separated pattern, such that in use said electrodes are essentially fixed in location with respect to one another such that confounding noise signals resulting from relative motion between said electrodes are reduced in use.

It is another purpose of the present invention to teach the use of variable resistor(s) in formation of a Wilson central terminal. The purpose thereof being to allow adjustment of a voltage appearing at a Wilson central terminal formed utilizing present invention Bioelectric Interface RA, LA and LL electrodes, so that it is within a desired range of deviation from a Wilson central terminal voltage obtained utilizing conventionally placed limb electrodes.

Other objectives and/or purposes will become apparent by refrence to the Specification.

BRIEF DESCRIPTION OF THE DRAWINGS

FIG. 2 shows a view of a two electrode bioelectric interface with a common adhesive sheet applied thereto, in which common adhesive sheet is present an electrically anisotropic property causing slit present between.

FIG. 7b shows a bioelectric interface configured for use with a twelve lead (ECG) system. Shown are groups of electrodes made of a plurality of electrode elements as shown in. FIG. 5b. Shown also are perforations in a continuous support sheet for use in detaching leads used in forming an Einthoven triangle Left Arm, Right Arm and Left Leg pattern.

FIG. 7d shows a bioelectric interface configured for use with a twelve lead (ECG) system. Indicated are electrodes positioned beneath paddles of a defibrillating system.

DETAILED DESCRIPTION

Discussion of FIGS. 8b and 10a–10e follows directly as they focus on advancements over the embodiments shown in the other figures which were first disclosed in application Ser. No. 09/374,873 filed Aug. 16, 1999, of which this Application is a CIP. As valuable background and depth is provided bu discusion of the FIGS. other than 8b and 10a–10e, discussion thereof is repeated herein, with minor amendment.

Figure 10A:
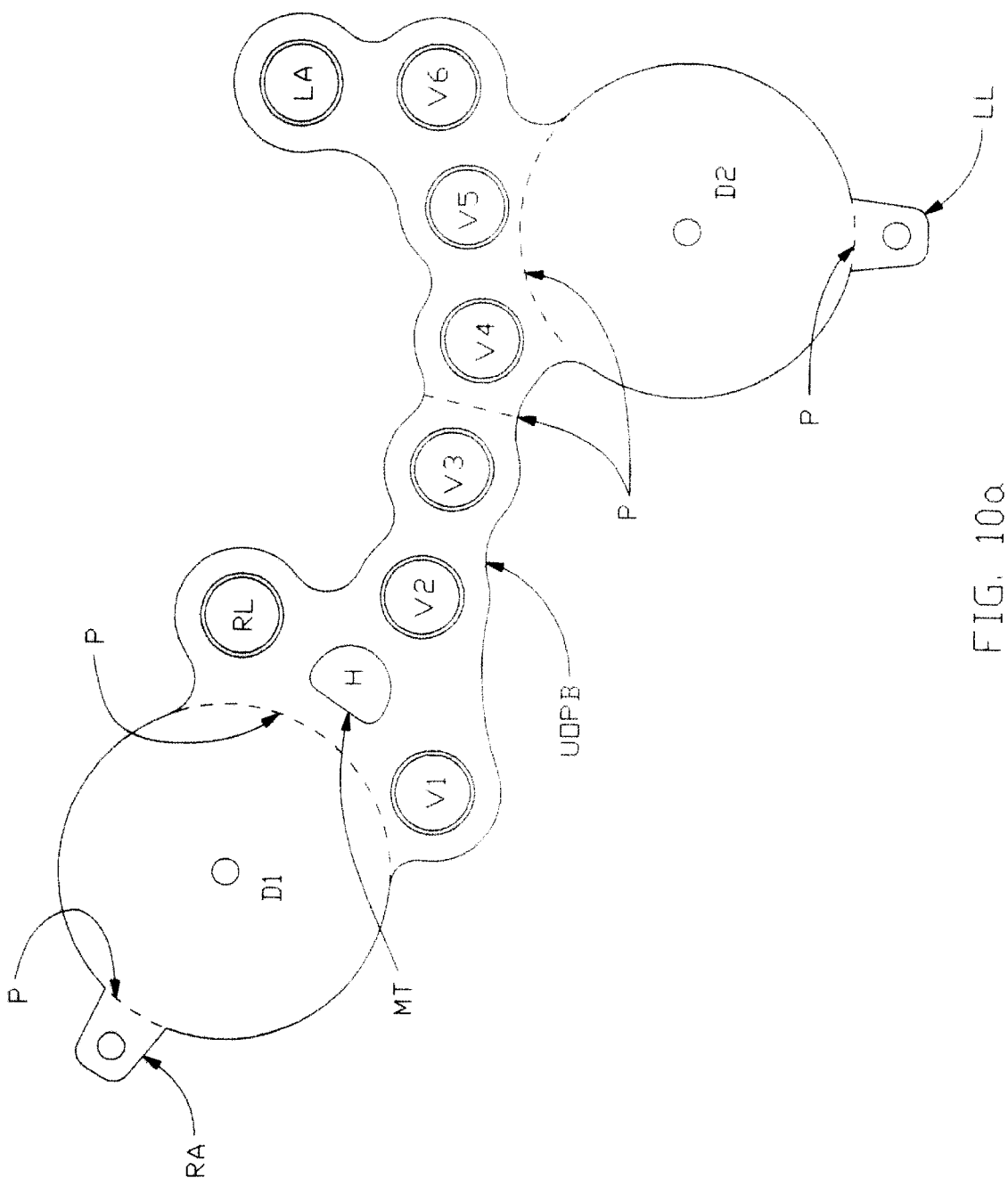
FIG. 10a shows an embodiment of the present invention bio-electric interface for application to a subject's chest during use, which is comprised of electrodes (D1) (D2) for applying defibrillation shocks, either as separate elements or integrated into said a bio-electric interface along with electrodes for monitoring ECG data.

Turning now to FIG. 10a an embodiment of the present invention bio-electric interface for application to a subject's chest during use, which is comprised of electrodes for applying defibrillation shocks, (D1) and (D2), integrated into said bio-electric interface, optionally via perforations (P) or by functional equivalents thereto. Also shown are precoridal electrodes for monitoring ECC data, (V1, V2, V3, V4, V5, V6) and the presence of right-arm (RA) and left-leg (LL) electrodes which are affixed to the defibrillation elements, again, optionally via perforations or functional equivalent thereto, such that detachment and deployment to conventional limb locations can be easily performed. Note that while electrodes for applying defibrillation shocks, (D1) and (D2), might be utilized in monitoring ECG data during application of a present invention bioelectric interface use, said electrodes for applying defibrillation shocks, (D1) and (D2), are dedicated for use in defibrillation in the present invention in the sense that ECG precordial monitoring electrodes (V1) (V2) (V3) (V4) (V5) and (V6) and limb lead forming electrodes (RA) (LA) and (LL) are not utilized in defibrillation.

Figure 7A:
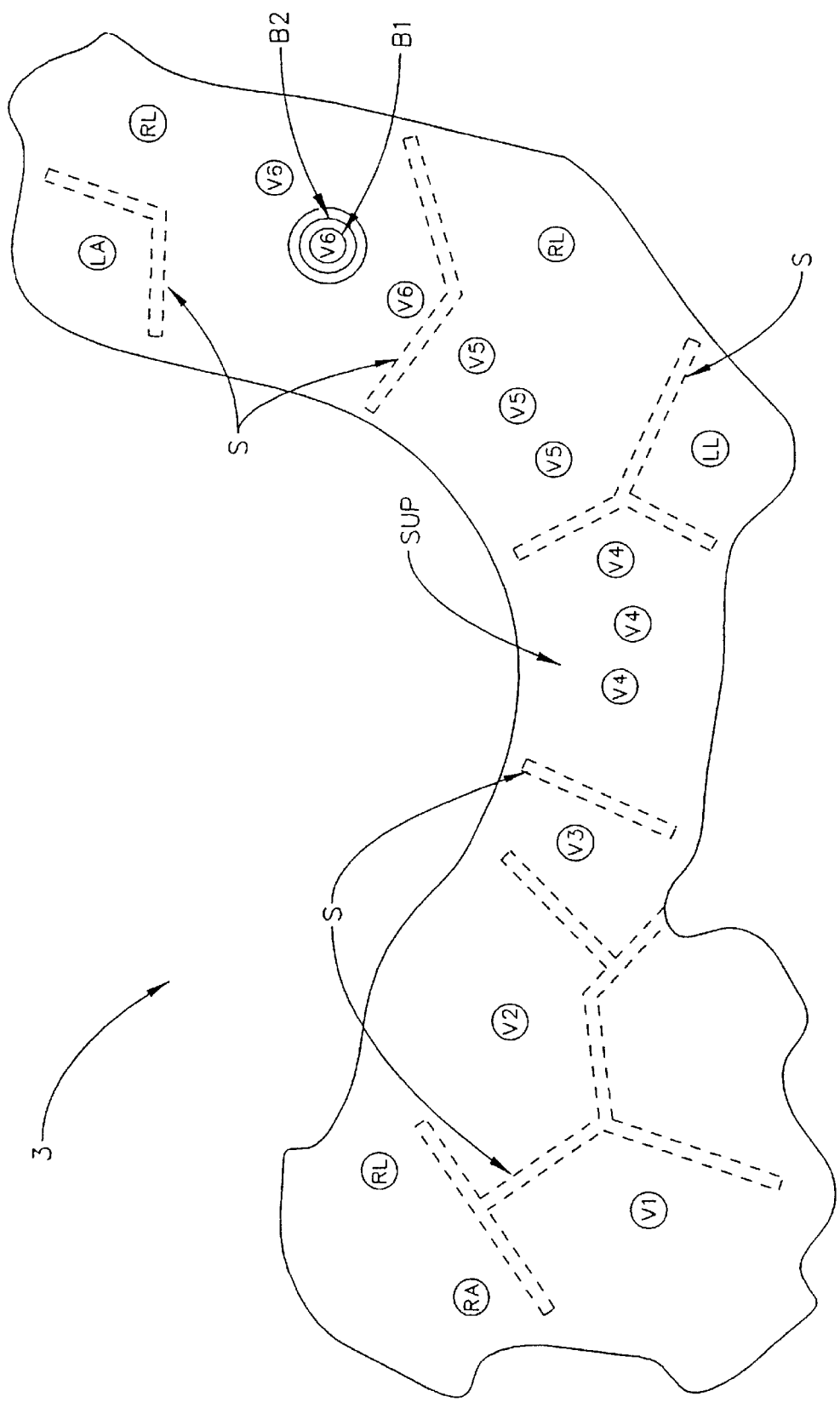
FIG. 7a shows a bioelectric interface configured for use with a twelve lead (ECG) system. Shown are groups of electrodes which serve to allow a "one-size to fit many" result. Also shown is an exemplary presence of a multi-element Bulls-eye electrode, and the presence of "slits" in an adhesive sheet to effect electrical anisotropic properties therein.
Figure 7B:
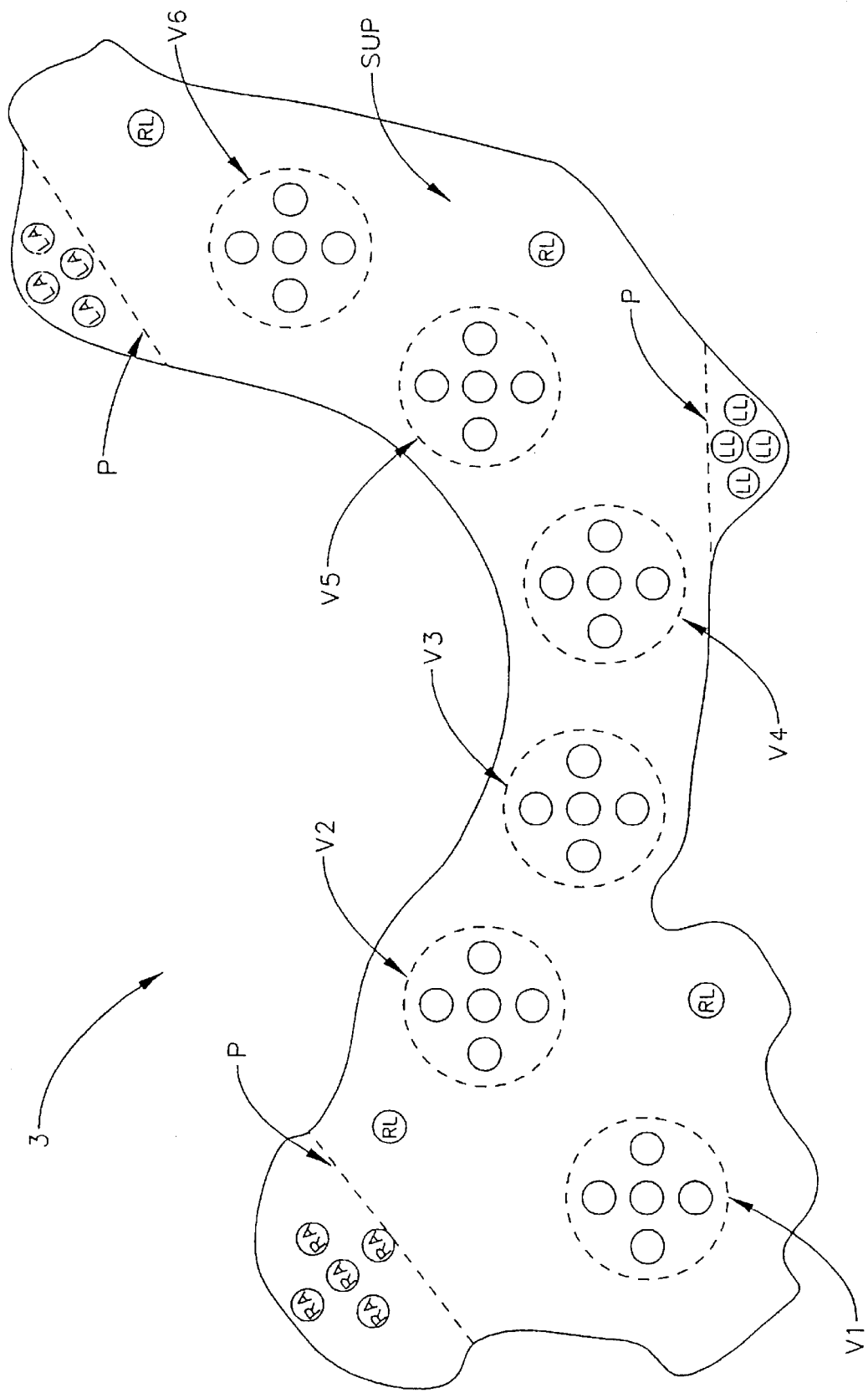
Figure 7C:
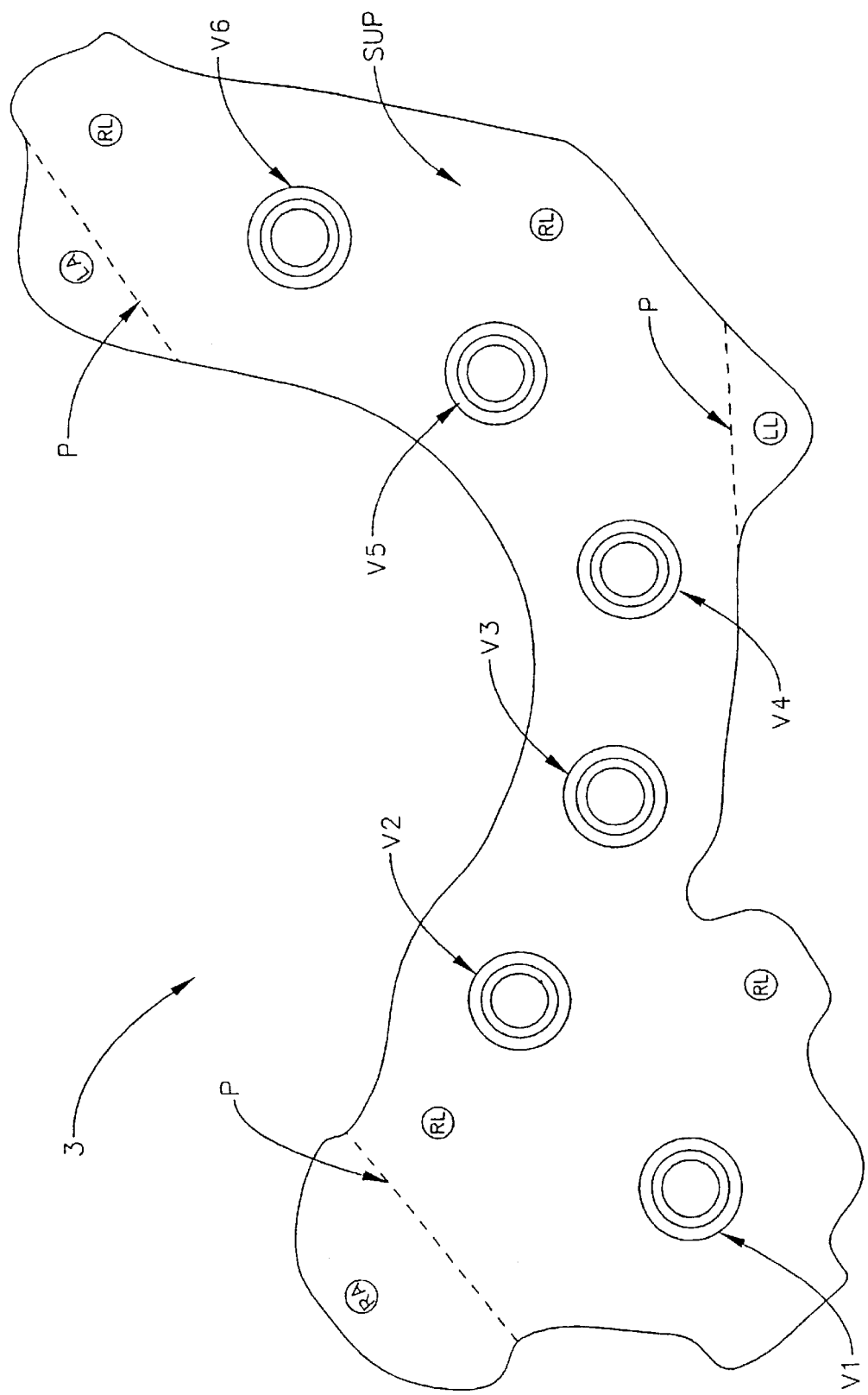
FIG. 7c shows a bioelectric interface configured for use with a twelve lead (ECG) system. Shown are groups of electrodes made of a plurality of electrode elements configured as shown in FIG. 5a, which serve to allow high frequency investigation and mapping. Shown also are perforations in a continuous support sheet for use in detaching leads used in forming an Einthoven triangle Left Arm, Right Arm and Left Leg pattern.
Figure 7E:
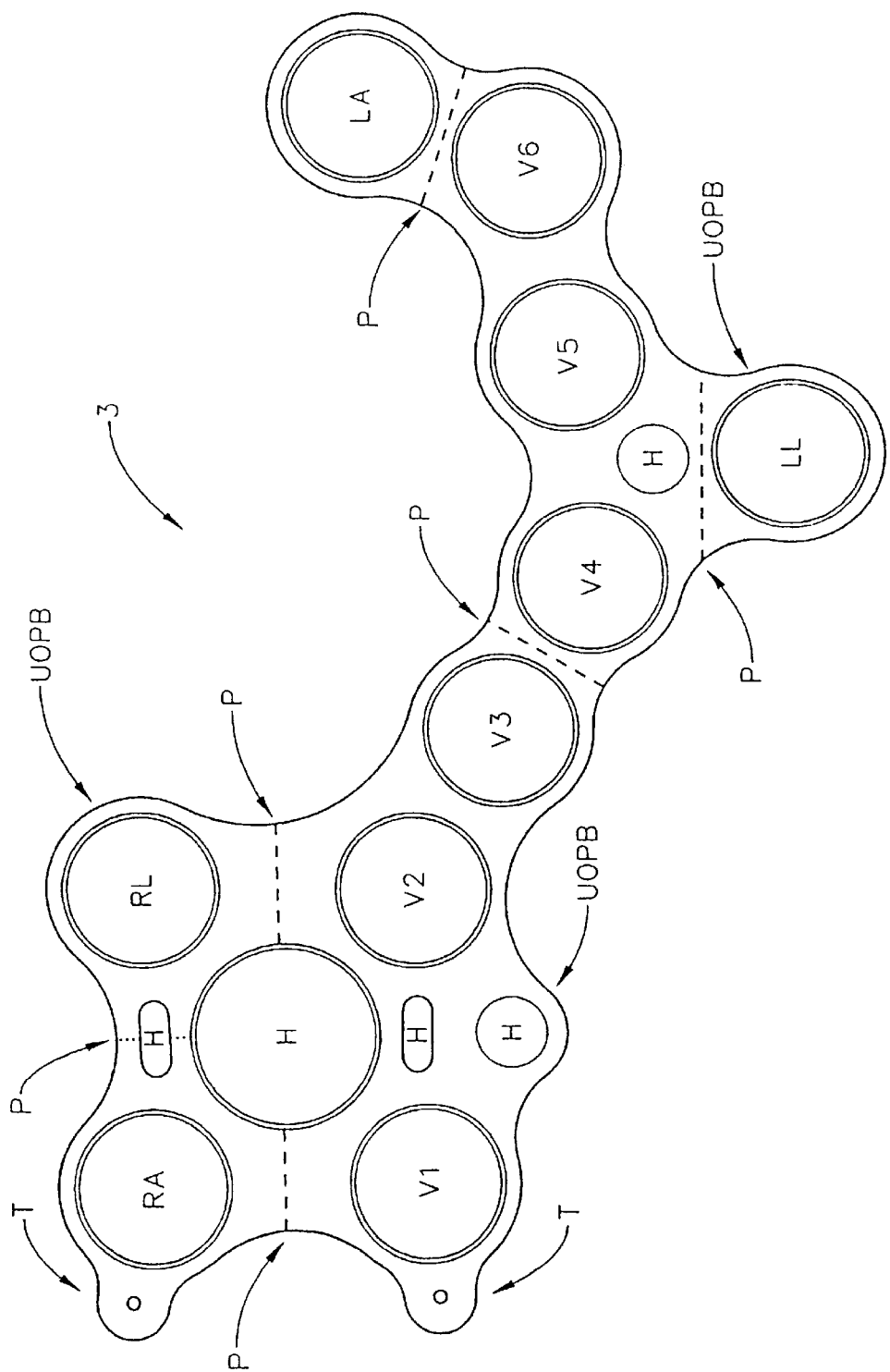
FIG. 7e shows a bloelectric interface with an undulated curved tab shaped outer edge, in combination with the presence of strategically placed holes through said bioelectric interface.
Figure 7F:
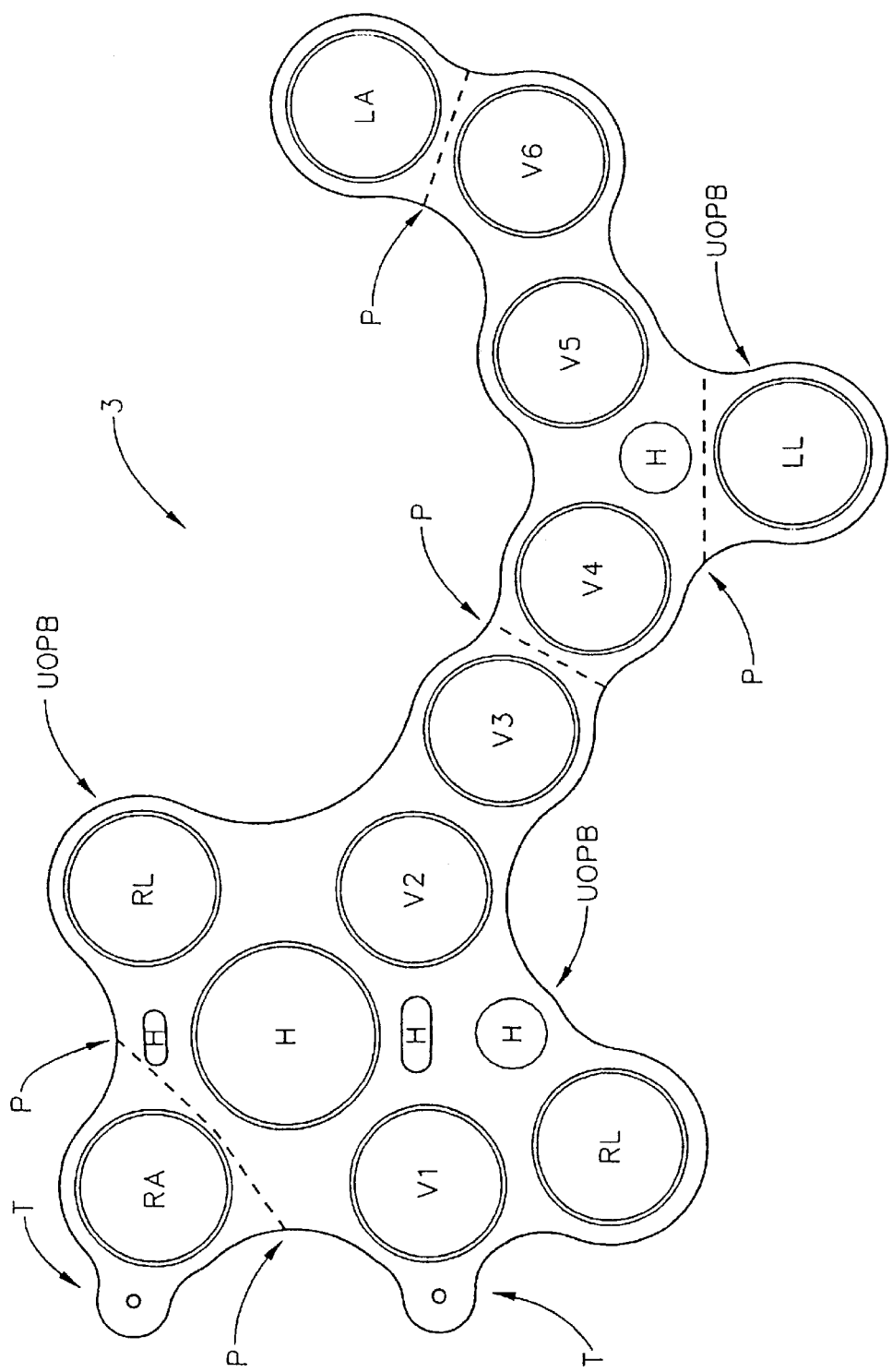
FIG. 7f shows a variation of FIG. 7e, in which the Right Leg (RL) electrode is positioned in an anatomically more familiar location.
Figure 10B:
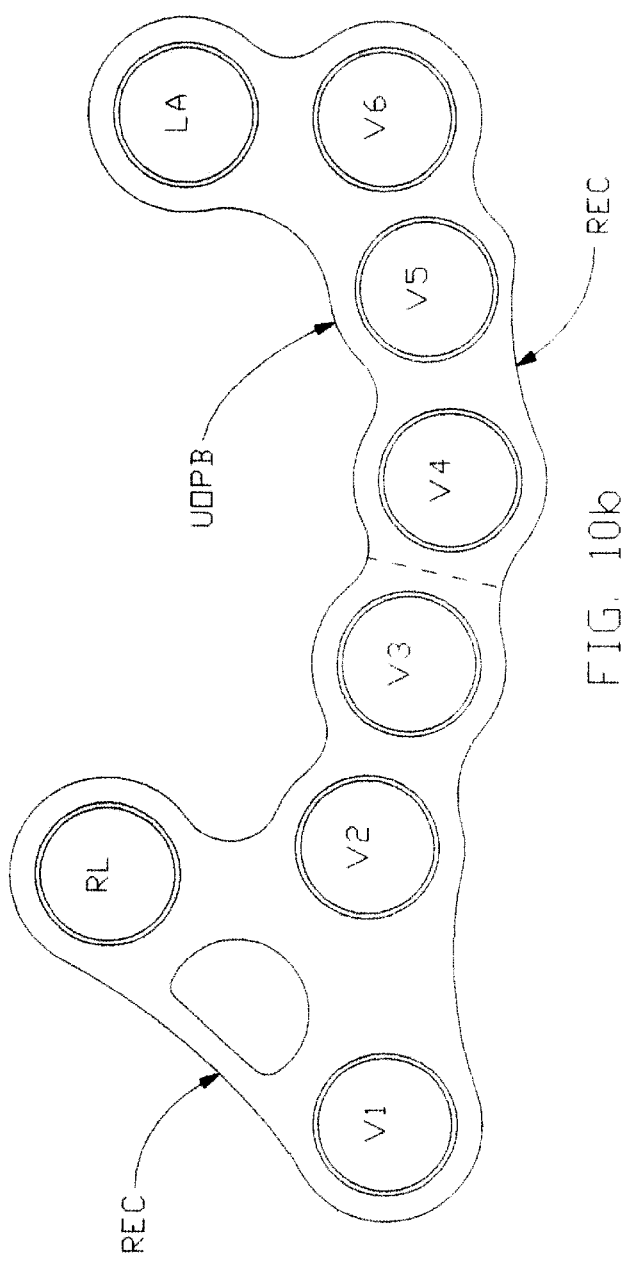
FIG. 10b shows the presence of an undulated outer edge (UOPB) which allows placement of independent element defibrillation electrodes (D1) and (D2) in the region of the right-arm and left-leg electrodes (identified generally as (REC), which right-arm (RA) and left-leg (LL) electrodes are shown present in FIGS. 7e and 7f.

FIG. 10b shows the presence of an undulated outer edge (UOPB) which allows placement of independent element defibrillation electrodes (D1) and (D2) in the region of the right-arm and left-leg electrodes (identified generally as (REC), which right-arm (RA) and left-leg (LL) electrodes are shown present in FIGS. 7e and 7f. Said defibrillation electrodes (D1) and (D2) are independent elements in this embodiment of the present invention bio-electric interface.

In use, where functionally appropriate, the defibrillation electrodes can be used as monitoring limb lead electrodes, or limb electrodes can be present on the defibrillation electrodes, as shown in FIG. 10*a* as (RA) and (LL). Note that the representation of (RA) and (LL) in FIG. 10*a* is to be interpreted sufficiently broad to include an electrode such as demonstrated at the left-arm (LA) location. That is, while "tab-like" electrodes are indicated at (RA) and (LL) locations, any functional electrode can be present thereat.

Note in FIG. 10*a* the presence of hole (H) in the region which appears over the Sternum when properly applied to a subject in use. It is to be appreciated that the shape of the hole (H.) is altered from circular, (see FIGS. 7*e* and 7*f*). What is represented is that material (MT) cut lose to form the hole, remains present at the straight left side of the hole (H) in FIG. 10*a*. Said remaining material serves as a tab which can be gripped in use to aid with application and removal of the present invention bio-electric interface.

Figure 10C:
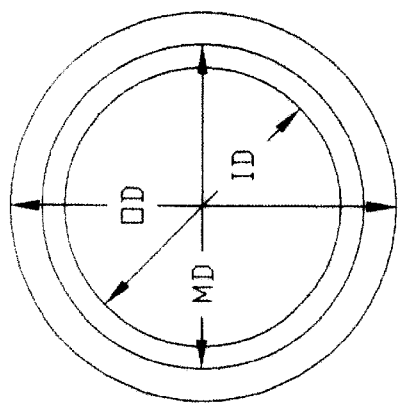
FIG. 10c shows a defibrillation electrode which is of a shape to fit snugly into the regions (REC) in FIG. 10.

Note that FIG. 10*c* shows a defibrillation electrode which is of a shape to fit snugly into the region in FIG. 10*b*, where analogically is present the right-arm (RA) or left-leg (LL) electrodes in FIGS. 7*e* and 7*f*. FIG. 10*c* shows an exemplary defibrillation electrode (D1) or (D2). Note that the outer diameter (OD) represents the backing materials, the smaller inner diameter (ID) the electrode current carrying material (s), and the mid-diameter (MD)demonstrates that a hydropolymer can extend beyond the current carrying materials within the inner diameter (ID). However, FIG. 10*c* is not limiting and any functional configuration can be utilized.

Again, FIG. 10*b* shows a present invention embodiment wherein the undulated edge is shaped to allow easy simultaneous presence of independent defibrillation electrode elements in functional combination with the ECG monitoring electrodes, but where the defibrillation electrodes are not affixed to the bio-electric interface. This can result from original manufacture or result where, in the field, the defibrillation electrodes are removed via separation at the perforations, or functional equivalents thereof.

It is to be appreciated that the defibrillation electrodes can be of other than circular shape and remain within the scope of the present invention bio-electric interface which comprises ECG monitoring electrodes (V1) (V2) (V3) (V4) (V5) and (V6), and defibrillation electrodes (D1) and (D2). The only criteria for determining sufficiency of a defibrillation electrode are such as having a large enough area to meet FDA and/or other guidelines, (eg. seventy-five (75) square centimeters per electrode or one-hundred-fifty (150) square centimeters total area for two electrodes, with neither being less than fifty (50) square centimeters), which area is many times greater than typical sensing electrodes, (which have an area on the order of one (1.0) centimeter square or less).

Figure 10D:
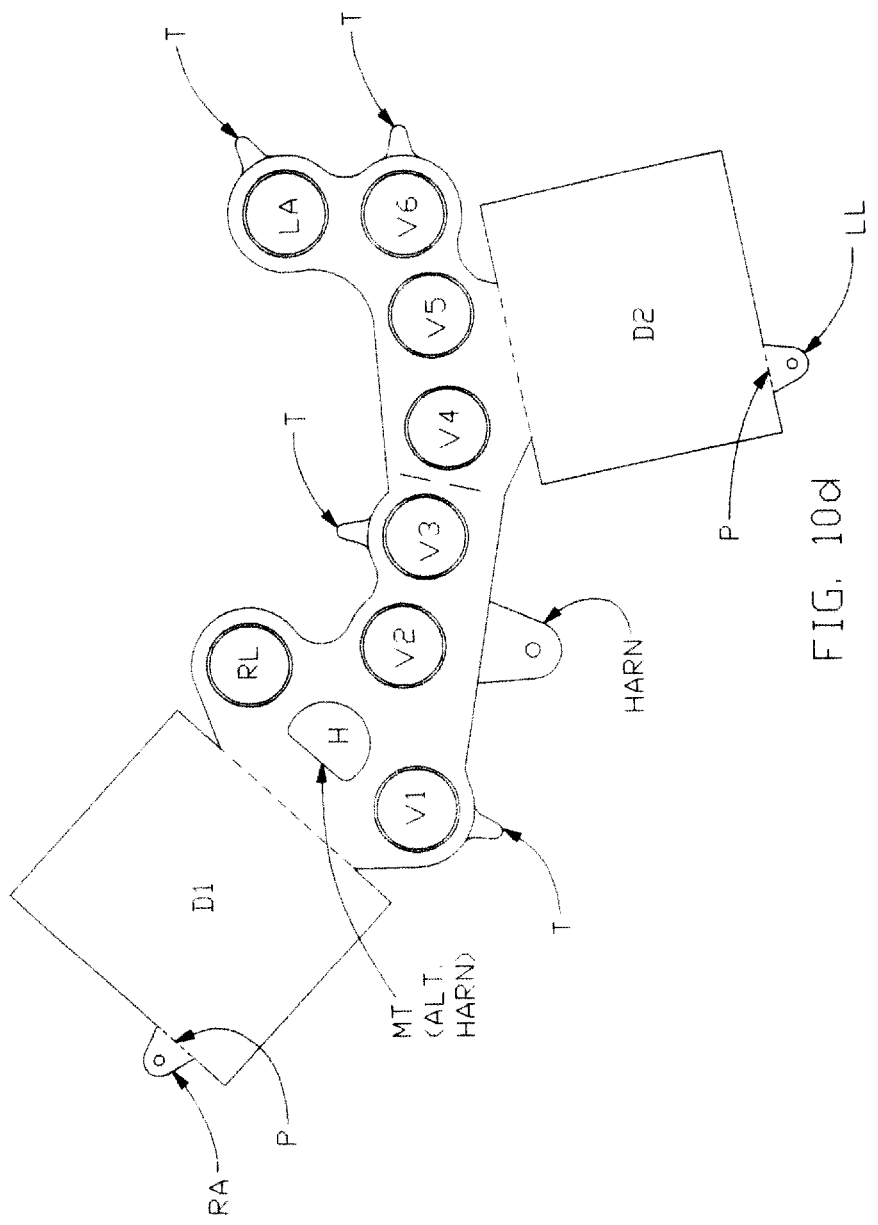
FIG. 10d is included to indicate that tabs (T) can be present at various locations of the present invention bioelectric interface to aid with gripping and positioning and/or removal to or form a subject, and that defibrillation electrodes which are of other than circular, but functional, shape can be utilized.

FIG. 10*d* is included to indicate that tabs (T) can be present at various locations of the present invention bioelectric interface to aid with gripping and positioning and/or removal to or from a subject. Further, defibrillation electrodes which are of other than circular shape are shown to indicate that any functional shape thereof is acceptable. In addition, it is to be fully appreciated that an outer edge of the remainder of the present invention bioelectric interface can be other than undulated, such as of the shape shown in FIGS. 7*a*–7*d*, or of any other functiona shape. That is, the present invention defibrillation electrods (D1) and (D2) can be applied to such as the FIGS. 7*a*–7*d* embodiments of a present invention bio-electric interface. While, as described elsewhere herein, an undulated outer edge (UOPB), or other general overall shape, can provide utility, such is not citical to establishing novelty the present invention combination of ECG monitoring precordial (V1) (V2) (V3) (V4) (V5) V6) and limb (RA) (LA) and (LL) electrodes and defibrillation electrodes (D1) and (D2).

Figure 10E:
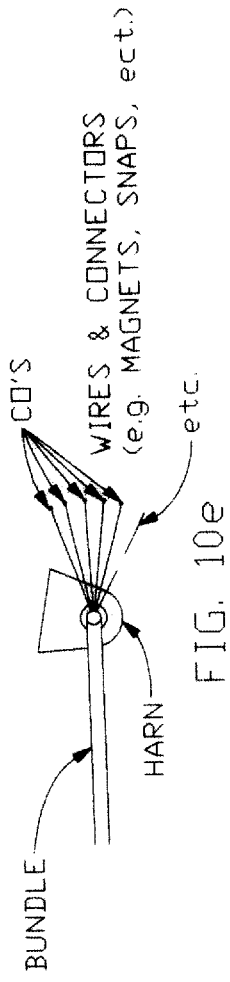
FIG. 10e demonstrates a bundle of wires being secured to the harness on a present invention bioelectirc interface, with indivudual wires therein being then separately accessible for attachment to appropriate electrodes beyond said harness.

FIG. 10*d* also shows the presence of a Harness (HARN). Said Harness is a tab which is present to allow securing a bundle of wires from ECG or defibrillation equipments, and thus act as a buffer to external forces being applied directly to electrodes via wire connections thereto. In use a wire bundle will be secured to said harness (HARN), and individual wires therein then attached onto appropriate electrodes. External forces will be primarily absorbed by said attachment of the wire bundle to said harness (HARN). FIG. 10*e* demonstrates a re-usable bundle of wires (BUNDLE) being secured to the FIG. 10*d* harness (HARN) on a present invention bioelectric interface, with individual wires in said bundle being then separately accessible for attachment, via connection means (CO's) to appropriate electrodes beyond said harness (HARN). Note that the harness (HARN) can be located adjacent to the hole (H) and made from material pulled away to form said hole (H), or at any functional location in FIG. 10*d*, or in a present invention in FIGS. 7*a*–7*ef*, 8*a*–8*b* 10*a*, 10*b* and 10*d* and modifications. Note that the connectors (CO's) can be snaps or magnets (where electrodes attached to are magnetic such as made of ferromagentic inks), or any functional means.

Generally, in FIGS. 10*a*–10*d*, it is to be understood that the shape and type, (eg. single or multi-element etc.), of electrodes present is not critical, other than as required to be functional. What is primarily new, novel, non-obvious and useful is the providing of ECG monitoring electrodes and defibrillation electrodes in a present invention bioelectric interface which can be conveniently affixed to a subject. In particular, electrodes in FIGS. 10*a*–10*d* are not to be interpreted as being limited to being any specific type of single or multiple element electrodes.

Figure 8A:
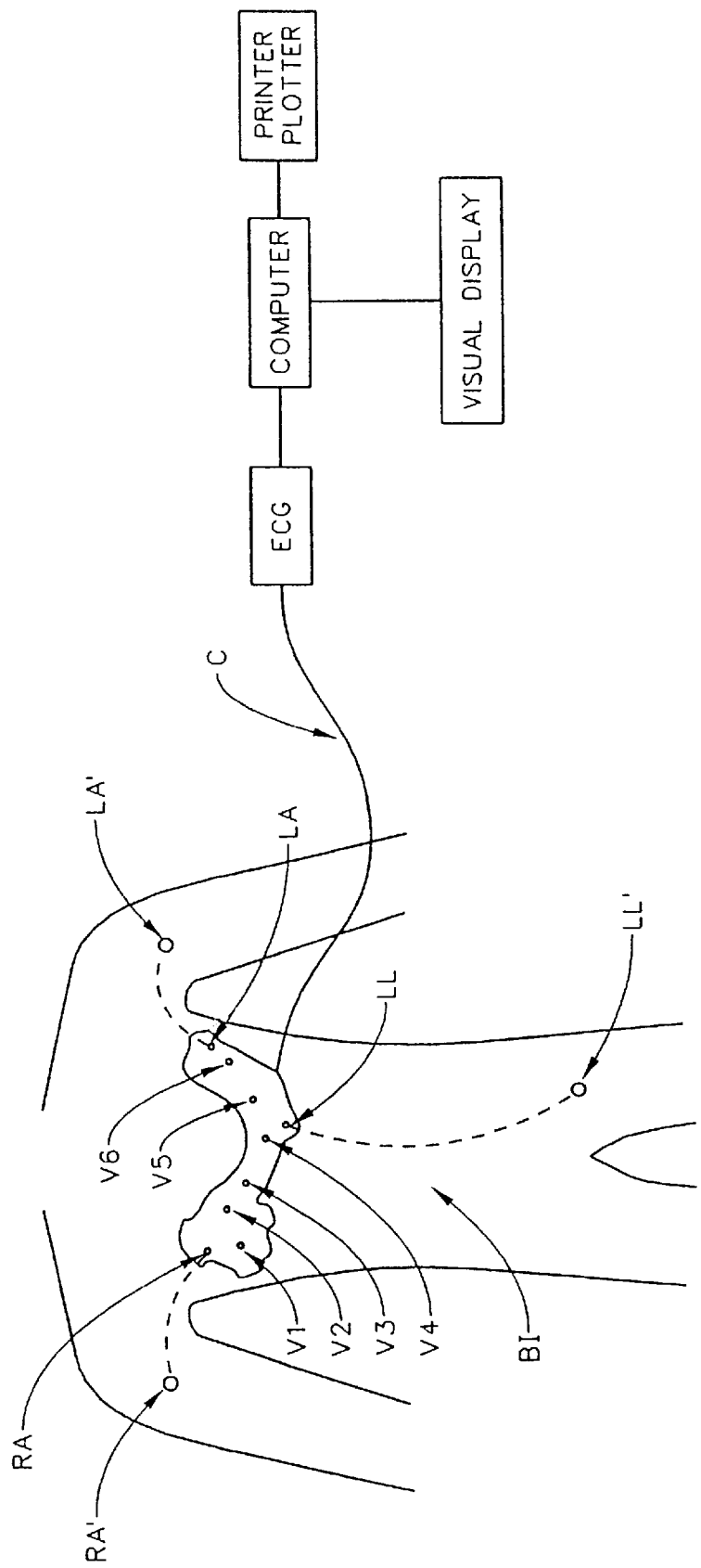
FIG. 8a generally exemplifies a system for utilizing an electrode patch (3) as shown in FIGS. 7a–7f. A computer system is shown situated to receive an (ECG) signal, and based thereupon cause a control system identified as (PACE/DEFIB) to provide electrical impulses to a subject via said electrode patch (3).
Figure 8B:
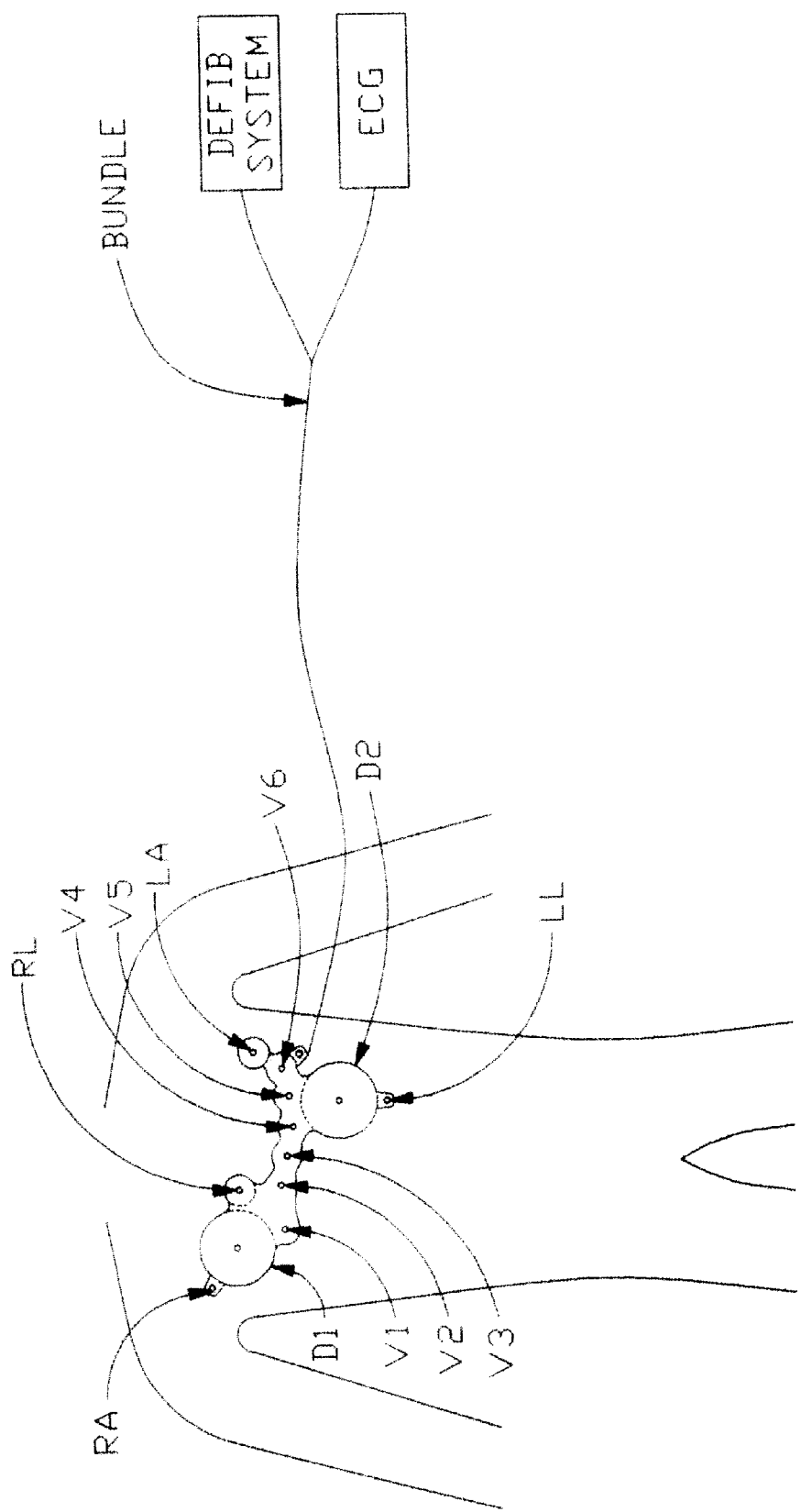
FIG. 8b shows a present invention bioelectric interface with defibrillation electrodes integrated thereinto, shown connected to a defibrillation system and ECG monitoring system.

FIG. 8*b* is also noted at this point as it shows a present invention bioelectric interface as in FIG. 10*a*, mounted on a subject. Note the presence of defibrillation electrodes (D1) and (D2) integrated thereinto, and the connection to a defibrillation system (DEFIB SYSTEM) via a bundle of wires (BUNDLE). Also shown is an ECG monitoring system much as shown in FIG. 8*a*.

Figure 1A:
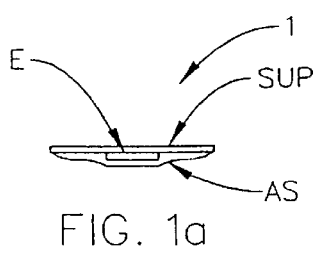
FIG. 1a shows a side elevational view of a bioelectric interface showing an electrode "sandwiched" by an adhesive sheet and a carrier matrix.
Figure 1B:
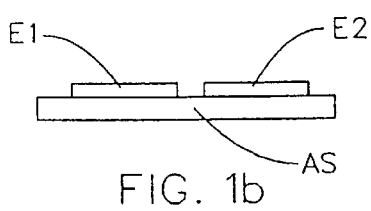
FIG. 1b shows a side elevational view of two electrodes situated on an adhesive sheet in essentially fixed relative positions with respect to one another.

Continuing, as described in co-pending application Ser. No. 09/374,873 filed Aug. 16, 1999, and repeated here for general background it is to be appreciated that FIG. 1*a*, shows a side elevational cross-sectional view of a single electrode (E) in a bioelectric interface (1) system comprising a Support Sheet (SUP) and an adhesive material (AS). Note that the electrode (E) is "sandwiched" between the Support Sheet (SUP) and adhesive material (AS). This is a typical arrangement, but where an adhesive material can provide sufficient spatial positioning integrity it is to be understood that the Support Sheet (SUP) can become unnecessary. FIG. 1*b* shows a side elevational view of two electrodes (E1) (E2) affixed to an adhesive sheet (AS) with a slit positioned therebetween.

Figure 2:
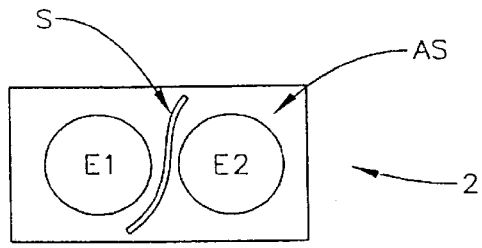

FIG. 2 shows a bioelectric interface system (2) comprised of two electrodes (E1) and (E2) looking from the surface thereof upon which is present an adhesive material (AS), (ie. that surface which will contact a subject's skin in practice). Note that a "slit" (S) is shown as present between said electrodes (E1) and (E2). In the case where the adhesive material is made of an electrically isotropic material, (eg. commercially available hydropolymers in sheet form for instance), it has been found that providing a slit (S) between two electrodes (E1) and (E2) effects essentially electrically anisotropic properties thereto. That is, a lower specific impedance will be measured from an electrode through the adhesive material than between two electrodes. In the case that an adhesive material provides such anisotropic electrical specific impedance properties, said slit (S) typically becomes unnecessary. It is noted that the reason the adhesive material should provide anisotropic electrical properties is that in an (ECG) setting, for instance, if the adhesive material is electrically isotropic, signals which should be present in one electrode in a bioelectric interface, will to some extent be present in other electrodes as well, as a result of lateral current flow through said adhesive material, and many prior multiple electrode systems therefore, enter an artifact to (ECG) data as a result. As well, adhesive material electrical anisotropicity allows use of higher resolution electrode geometry, (discussed supra) because lateral current flow is limited.

It will be noted that the adhesive material (AS) in FIG. 2 is not completely bisected by the slit (S). This is a preferred, but not limiting practice, because complete electrode isolation is not always optimum. For instance, in (ECG) system settings it is common to inject a noise compensating signal to a Right Leg electrode via a driver circuit, which signal is to be imposed upon all electrodes. This practice is well known by practitioners in the (ECG) field, with noise compensating current flow normally being through a subject's skin, but it has been found that allowing some electrical path through the adhesive material does not noticeably degrade acquired (ECG) data. With that thought in mind it is noted that a goal of the present invention is to provide a very firm affixation to a subject's body such that spatial separation between electrodes is maintained constant and such that good electrical contact between electrodes and a subject's skin is effected, via said adhesive material. Hence, the more surface area of the present invention bioelectric interface upon which the adhesive material remains present, the better.

Figure 3A:
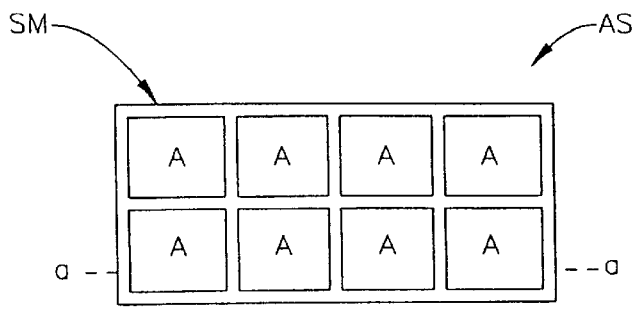
FIGS. 3a and 3b show top and side elevation views respectively of a novel electrically anisotropic adhesive sheet.

FIG. 3a shows a present invention system for providing electrically anisotropic specific impedance in an "adhesive sheet". Shown is an electrically non-conductive "Scrim" (SM) present in a form which provides numerous channel regions, said channel regions being filled with electrically isotropic conductive adhesive material (A).

Figure 4A:
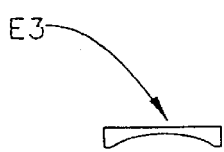
FIGS. 4a and 4b show various designs for electrodes.
Figure 4B:
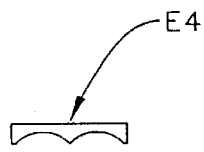
Figure 4C:
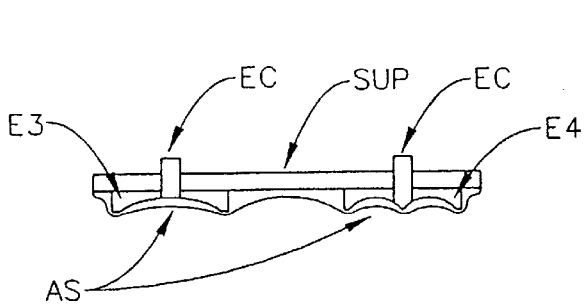
FIG. 4c shows the electrodes of FIGS. 4a and 4b between a carrier matrix and adhesive sheet including a cocklebur structure means.

Turning now to FIGS. 4a and 4b, there are shown preferred shapes (E3) and (E4) for electrodes. Note that there are regions of said electrodes which will tend to project into an adhesive material (AS) placed in contact therewith. The effect of said projection is to provide a thinning of the adhesive material (AS) and effect an electrically anisotropic character to the adhesive material (AS) as viewed in cross section. That is, electrical impedance from an electrode (E3) or (E4) through said adhesive material (AS) will be caused to be less than that between electrodes (E3) and (E4) through said adhesive material (AS), because of a thinning effect at the projecting edges of said electrodes. FIG. 4c demonstrates what can be described as a "cocklebur structure means" in an electrode wherein the projection (E4) serves to provide subject electrical contact improvment, perhaps even projecting through the adhesive material (AS). FIG. 4c also shows the presence of external device electrical connector means (EC).

Figure 5A:
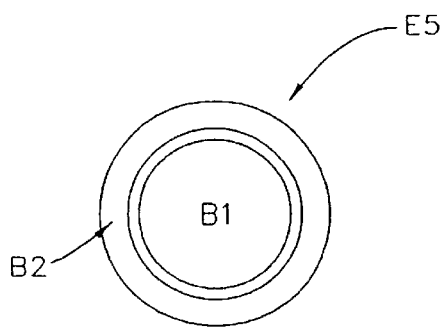
FIG. 5a shows a multi-element electrode configured in a Bulls-eye pattern.
Figure 5B:
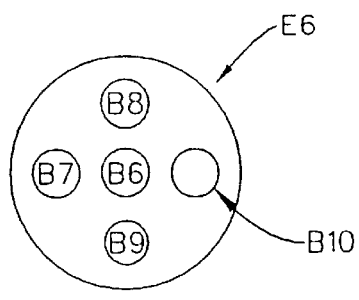
FIG. 5b shows a multi-element electrode pattern configured from button electrodes.

FIG. 5a shows an example of a multi-element electrode (E5) with a "Bulls-eye" geometry. As described in the Disclosure of the Invention Section of herein, use of said multiple element electrodes allows investigation of high frequency components in (ECG) signals, and allows better spatial resolution of the sources of monitored (ECG) signals. (It is to be understood that the "Bulls-eye" shape is an example of a multi-element electrode, and that any functionally similar multi-element electrode configuration is to be considered as included within the term "Bulls-eye"). The underlying distinction between multi-element electrodes and single element electrodes being that multiple single element electrodes typically utilize a single common electrode as a reference, whereas multi-element electrodes provide their own reference point. It will be appreciated that electrical anisotropicity can become very important in view of the higher resolution capability of "Bulls-eye" electrodes, when signals are being monitored from closely positioned points of, for instance a human heart muscle. That is, greater resolution capability is of no consequence if the signal reaching a sensing electrode is effected by lateral current flow through an attached adhesive material, which signal was originated by a distal source. FIG. 5b shows a plurality of "Button" electrode elements (B6), (B7), (B8), (B9) and (B10) which comprise an electrode (E6). Such an arrangement is beneficially utilized in a present invention Bioelectric Interface-meant for use in Defibrillation. The well known "Edge" effect which results in uneven current distribution over the region of an electrode can be reduced by such a configuration.

Figure 6A:
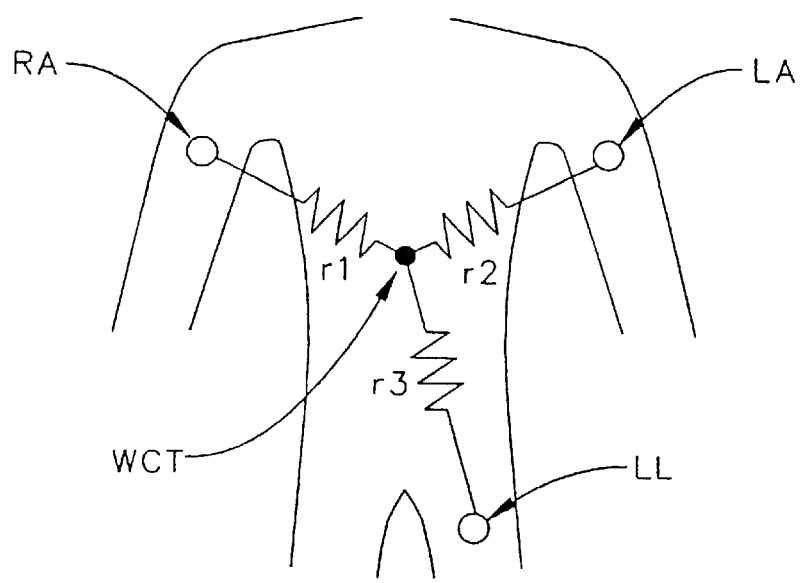
FIG. 6a shows a partial frontal view of a human torso, with formation of a Wilson Central Terminal from standard RA, LA and LL electrodes indicated.
Figure 6B:
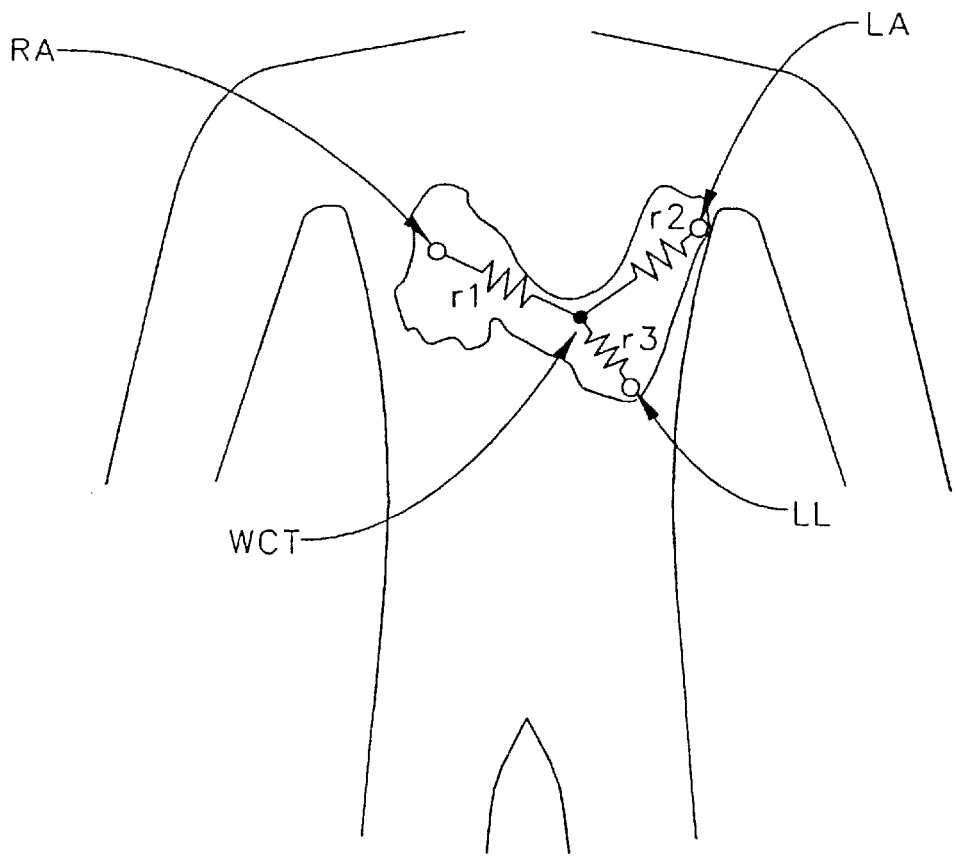
FIG. 6b shows a partial frontal view of a human torseau, with formation of a Wilson Central Terminal indicated, as formed from chest mounted RA, LA and LL electrodes of the present invention bioelectric interface.

FIG. 6a shows a partial human torso with RA, LA and LL electrodes placed on the limbs. Also shown is an Einthoven triangle Wilson Central Terminal (WCT) formed by attaching resistors to said RA, LA and LL electrodes, which resistors have a common central connection so as to form a "Y" circuit. FIG. 6b shows a partial human torso with RA, LA and LL electrodes placed on the chest as is effected by the present invention Bioelectric Interface (3). Also shown is an Einthoven frontal I, II, III lead triangle,.Wilson Central Terminal (WCT) formed by attaching resistors (r1), (r2) and (r3) to said RA, LA and LL electrodes, which resistors have a common central connection so as to form a "Y" circuit. (Note, in use, the (WCT) voltage serves as a reference for precordial leads from V1, V2, V3, V4, V5 and V6 as are described elsewhere herein, for the FIGS. 6a and 6b cases, and equivalence thereof in both cases allows acquiring familiar precordial ECG data from both).

It is the result of the present invention that voltages which appear at Wilson Central Terminals shown in FIGS. 6a and 6b, each with respect to a reference, are within some acceptable variance, (eg. 1.0 millivolt), therebetween, if the present invention RA, LA and LL electrodes are appropriately positioned within the FIG. 6b demonstrated bioelectric interface. A method of accomplishing this can be aided by causing at least one of the RA, LA and LL electrodes to be comprised of a plurality of electrically independent electrode elements, (as demonstrated in FIG. 7b). A user can, manually or via automation, optimally select an element in each RA, LA and LL electrode. As well, resistances (r1, r2 and/or r3), can be variable and a user can vary one or more of them.

Turning now to FIG. 7a there is shown an-approximately "actual size" typical present invention bioelectric interface system (3) with electrodes present therein and appropriately spatially distributed and positioned for use with a twelve lead (ECG) system. FIG. 7a shows the surface of the present invention bioelectric interface (3) opposite to that upon which is typically present an adhesive material which contacts a subject's skin in use. In use the bioelectric interface system (3) will typically be placed upon a subject's chest with the various precordial V1–V6 electrodes, and electrode groups, placed as follows:

electrode V1—in the region of the fourth intercostal space at the right sternal border.

electrode V2—in the region of the fourth intercostal space at the left sternal border;

electrode V4—in the region of the fifth intercostal space at the left mid-clavicular line;

electrode V3—in the region half way between electrodes V2 and V4;

electrode V5—in the region of the fifth intercostal space at the left anterior axillary line; and electrode V6—in the region of the fifth intercostal space at the left mid-axillary line.

Note that electrodes V4, V5 and V6 are each shown as a group of electrode elements. The present invention provides for any of the electrodes V1–V6 and any other electrodes which might be present, to be present as a group thereof. The reason for this is that the present invention bioelectric interface is, to some extent, a "single size fits many". That is, even though subject's body sizes vary greatly one to another, the present invention can be applied to essentially any non-deformed subject and an electrode within a group of electrodes in the region of an appropriate location will be found to be properly positioned for use, within an error which exists even if individual electrodes are utilized, (said error originating from improper application of a single electrode). It is emphasized that while only V4, V5 and V6 precordial electrodes are shown as groups of electrode elements in FIG. 7a, any electrode shown, or any other configuration of electrode elements utilized, can be present as a group of electrodes as necessary to effect the "one-size-fits-many" feature of the present invention bioelectric interface system. The reason that FIG. 7a shows electrodes V1, V2 and V6 as single electrodes and electrodes V4, V5 and V6 as shown as groups of electrode elements is that, in practice, application of the present invention bioelectric interface system to a subject's body will proceed in a manner that typically assures appropriate positioning of electrodes V1, V2 and V3 on a subject's chest. The remaining electrodes will then make contact with the subject's body at locations based upon the size and shape of the bioelectric interface (3), which for any specific electrode might or might not be at the generally accepted locations recited infra. Where a group of electrodes is present, however, it should be appreciated that one of the electrodes in the group will be found to be more appropriately positioned than the others of the group. It is also noted that where groups of electrodes are present, unused electrodes in a group can be utilized as, for instance, electrodes to effect cardiac-pacing. As well, if one electrode in a group becomes inoperable, another can be substituted and still allow acquisition of reasonable (ECG) data. (See FIGS. 7b and 7c for other non-limiting examples). Also, multiple electrodes can be combined in a parallel configuration to allow greater current carrying capability during, for instance, defibrillation procedures.

Shown also in FIG. 7a are also the Right Arm (RA), Left Leg (LL) and Left Arm (LA) electrodes, positioned as appropriate for use as an Einthoven triangle configuration pattern, and for use as Right Arm (RA), Left Leg (LL) and Left Arm (LA) electrodes in the present invention bioelectric interface. Said electrodes can, but need not necessarily, be positioned as:

electrode (RA)—in the general region of the first or second intercostal space to the right of the sternam;

electrode (LA)—in the general region of the left third or fourth intercostal space at the mid-axillary line; and electrode (LL)—in the general region of the inferior costal margin between the right or left mid-clavicular lines.

(Note, multiple electrodes designated Right Leg (RL) are also present. As alluded to above, the Right Leg (RL) electrode in (ECG) settings is typically utilized to inject an out-of-phase noise compensating signal, which can be functionally applied to many electrodes. It has been determined that said noise compensating signal can be injected at any essentially any location on the present invention bioelectric interface without degradation of the results. Note also that the electrodes positioned for use as Right Arm and left Leg electrodes can be larger, suitable for use as Defibrillation Electrodes).

Figure 3B:
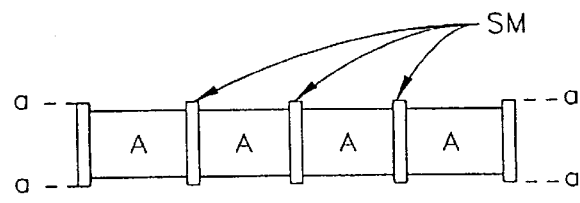

Also note that slits (S) in an electrically isotropic adhesive material are shown in broken lines. As viewed, said adhesive material would be present on a lower surface of the shown present invention bioelectric interface (3), hence are shown as viewed through the adhesive material and indicated Support Sheet (SUP). Said slits (S) will be less necessary, and probably unnecessary, where an adhesive material constructed from an inherently electrically anisotropic material, such as demonstrated by FIGS. 3a and 3b, is utilized. In such systems the scrim (SM) can provide structural integrity, while the present electrically conductive adhesive can provide sufficient adhesive contact and electrical conductivity.

Also note that FIG. 7a shows one of the V6 electrodes as a "Bulls-eye" electrode with a central Button (B1) and outer annular ring (B2) present. Again, this is demonstrative, and in effect all electrodes could be of a multi-element construction. The conductive polymer will typically, though not necessarily, be discontinuous between the element of a multi-element electrode. Note than the central Button (B1) can still serve as a standard Button electrode. In use, one could also interconnect the V6 (B1) and (B2) elements, or all the electrodes in a group, (for instance, if it became necessary to defibrillate a subject while a present invention bioelectric interface is in place). Conventional practice would require removal of any such electrode providing system. However, where the present invention bioelectric interface (3) is present, a defibrillation paddle could be positioned to effectively form a single electrode from electrodes in the V4, V5 and V6 groups. (Note said defibrillation paddle could contact external contact means (EC) such as shown in FIG. 4c). A second defibrillation paddle could likewise be simultaneously applied to the V1, V2 and V3 electrodes, or group of electrodes should alternatives be present at V1, V2 and V3 electrode locations. (See FIG. 7d for indication of Defibrillation Paddles in use).

Again, FIG. 7a provides a non-limiting example of a Bioelectric Interface (3) of the present invention. The present invention is, however, in the combination of the various disclosed elements thereof, in their various forms, as well as in electrode positioning.

Continuing, FIG. 7b shows a present invention Bioelectric Interface (3) with electrodes consisting of a FIG. 5b electrode element arrangement present at all V1, V2, V3, V4, V5 and V6 locations in the Support Sheet (SUP). RA, LA and LL electrodes are also shown to comprise multiple electrode elements. As in FIG. 7a, the Bioelectric Interface is viewed from the non-subject contacting side, and indications of the presence, and positioning of electrodes electrically accessible from both the shown, and subject contacting sides is present. The dotted lines surrounding each of said V1, V2, V3, V4, V5 and V6 locations is to indicate that the FIG. 5b electrode element arrangement is to be taken in combination as an electrode. Also note that FIG. 7b shows Perforations (P) present in the Support Sheet (SUP) at electrode RA, LA, and LL, (eg. Right Arm, Left Arm and Left Leg) locations. Said Perforations (P) allow easy removal of the RA, LA, and LL electrodes when it is desired to deploy and place said electrodes at conventional subject limb locations in use.

FIG. 7c shows a present invention Bioelectric Interface (3) with FIG. 5a Bulls-eye electrodes present at V1, V2, V3, V4, V5 and V6 locations in the Support Sheet (SUP). As in FIGS. 7a and 7b, the Bioelectric Interface is viewed from the non-subject contacting side, and indications of the presence, and positioning of electrodes electrically accessible from both the shown, and subject contacting sides is present. Also note that FIG. 7c, as did FIG. 7b, shows Perforations (P) present in the Support Sheet (SUP) at electrode RA, LA, and LL (eg. Right Arm, Left Arm and Left Leg) locations. (Said term "Perforations (P)" is to be interpreted to include functionally equivalent means which enable easy removal of the RA, LA, and LL electrodes when it is desired to deploy said electrodes at conventional limb locations in use).

FIG. 7d shows a present invention Bioelectric Interface (3) with simple single Button electrodes present at V1, V2, V3, V4, V5 and V6 locations in the Support Sheet (SUP). As in FIGS. 7a, 7b and 7c, the Bioelectric Interface is viewed from the non-subject contacting side, and indications of the presence, and positioning of electrodes electrically accessible from both the shown, and subject contacting sides is present. Also shown are outline representations of First (DF1) and Second (DF2) Defibrillation Paddles placed over the RA, LA, LL, V1, V2, V3, V4, V5 and V6 electrodes of the present invention Bioelectric Interface (3), as said First (DF1) and Second (DF2) Defibrillation Paddles would be positioned in use. Note that First (PD1) Defibrillation Paddle electrically contacts electrodes RA, V1, V2, and V3, while Second (DF2) Defibrillation Paddle electrically contacts electrodes LA, LL, V4, V5, and V6. The multiple points of supply of electrical energy to the body of a subject wearing the present invention Bioelectric Interface (3) serves to reduce uneven current flow caused by electrode "Edge" effect. It should be appreciated that were First (DF1) and Second (DF2) Defibrillation Paddles shown applied to FIG. 7b or 7c, even more separate electrode elements would be contacted, and the "Edge" effect would be even more reduced.

The Defibrillation Paddles (DF1) and (DF2) of FIG. 7d can, of course, be placed on the equivalent electrode groupings in FIG. 7f:

((RA) ((RL) (V1) (V2) (V3)); and
((LL) (V4) (V5) (V6) (LA)) as well;

or said electrodes in each grouping otherwise paralleled. Note in particular how the Perforation (P) in FIG. 7f then enables easy separation of said electrode groupings.

As a general comment regarding FIGS. 7a, 7b, 7c and 7d, the electrodes are shown positioned in each Bioelectric Interface (3), as viewed from the non-subject contacting side thereof. FIG. 4c demonstrates the typically only an external device electrical connector means (EC) is visible as so viewed, with a typically larger electrode area present on the subject contacting side. Hence, FIGS. 7a, 7b, 7c and 7d should be viewed as demonstrating the positioning of electrodes, and elements which comprise them, in a present invention Bioelectric Interface, rather than being accurate representations of the size of said electrodes, as viewed.

Turning now to FIG. 7e, there is shown a prefered embodiment of the present invention bioelectric interface (3). Shown are a support sheet (SUP) in functional combination with at least nine (9) spatially separated electrocardiogram system electrodes, each of said at least nine (9) spatially separated electrocardiogram system electrodes, which can be of a construction selected from a group consisting of: (a single electrical electrode element and a group of electrically independent electrode elements). Each of said spatially separated electrocardiogram system electrode is affixed to said support sheet (SUP) in a manner such that the relative positions of said electrocardiogram system electrodes with respect to one another are essentially fixed therewithin. Nine (9) of said at least nine (9) electrocardiogram system electrodes are configured in an RA, LA, LL, V1, V2, V3, V4, V5, V6 electrocardiogram system electrode pattern much as described with respect to FIGS. 7a–7d. The prefered embodiment is shown to also include an electocardiogram system RL electrode. In particular it should be noted that the FIG. 7e embodiment further comprises perforations in said support sheet (SUP) which allow easy detachment and deployment of at least one of said electrocardiogram RA, LA, LL and RL electrodes, thereby allowing positioning at a location selected from the group consisting of: (in contact with a subject's chest, and in conventional subject limb position). Further note that fold enhancing impression and/or perforations are shown as present between V3 and V4 electodes, and between RA and V1 electrodes. Such fold enhancing impression and/or perforations can be present between essentially any at two electrodes such as between V1 and V2; V2 and V3; V3 and V4; V4 and V5; V5 and V6; RA and V1; V4 and LL; LA and V6. As with other embodiments in said FIG. 7e prefered embodiment, the support sheet is at least partially covered with an adhesive material on a subject contacting side thereof, and said adhesive material can present with electrical conductive properties selected from the group consisiting of: (isotropic electrical conductive properties, and anisotropic electrical conductive properties such that the regional specific impedance through said adhesive material is less than in a laterally oriented dimension direction therealong). Also, said adhesive material can be hydrophillic and non-hydrophillic and partially hydrophillic and partially hydrophobic. Note also that the bioelectric interface in FIG. 7e has at least one hole (H) present through said support sheet at a location between electrodes, which hole allows access to a subject's skin in use. Holes (H) are shown at location of the level of the second intercostal space adjacent to said RA electrode, and at the level of the fourth intercostal space adjacent to said VI electrode, and between said RA and V2 electrodes, and between said V4 and V5 electrodes. Such holes make the bioelectric interface more compliant and able to conform to a subject's body contours. Also note that the FIG. 7e bioelectric interface has an "undulated" outer perimeter boundary shape. This is prefered as it further enhances conformation to a subject's body contours in use, and said "undulations" allow relatively easy grasping between a thumb and first finger, thereby facilitating removal of a bioelectric interface from a subject, (which has proven a bit difficult with some bioelectric interfaces without an "undulated" outer perimeter boundary. FIG. 7f shows a variation of FIG. 7e, in which the Right Leg (RL) electrode is positioned in an anatomically more familiar location. It is noted however, that the Right Leg (RL) electrode is utilized only for entering noise cancelling signals, hence can be located essentially anywhere in the bioelectric interface (3).

As a general comment regarding FIGS. 7a, 7b, 7c, 7d, 7e and 7f, the electrodes are shown positioned in each Bioelectric Interface (3), as viewed from the non-subject contacting side thereof. FIG. 4c demonstrates the typically only an external device electrical connector means (EC) is visible as so viewed, with a typically larger electrode area present on the subject contacting side. Hence, FIGS. 7a, 7b, 7c, 7d, 7e and 7f should be viewed as demonstrating the positioning of electrodes, and elements which comprise them, in a present invention Bioelectric Interface, rather than being accurate representations of the size of said electrodes, as viewed.

As another general comment, it is to be appreciated that the present invention bioelectric interface system provides a means by which many electrodes can be applied to a subject by a simple, error limiting procedure. As it is generally accepted that improper application of electrodes is the most common reason for faulted (ECG) data acquisition, this is significant. As well, the present invention bioelectric interface provides a rather significant body contact surface area, said surface area being, typically, essentially covered with an adhesive material. This serves to ensure that electrodes, once applied to a subject, will not vary from the positions in which they are applied, and should not vary with respect to one another. It is known that relative motion between electrodes accounts for production of noise in acquired (ECG) data. The present invention greatly limits problems associated with noise generated by this effect. In fact, it is generally possibly to perform cardio-pulmonary-resuscitation on subjects wearing the present invention bioelectric interface while continuing to acquire (ECC) data. It is also mentioned that when the adhesive material is a hydropolymer, subject discomfort is minimized, and moisture resulting from sweating etc. actually serves to improve the adhesion properties.

While not shown, it is possible to form arrays of electrodes in a present invention bioelectric interface, for use in cardiac mapping. In such arrays, electrode arrangement is typically rectangular with, for instance, sixteen, twenty-four, thirty-six, sixty-four etc. electrodes present. The electrodes present can be of Button or Bulls-eye geometry, or, in other embodiments of the present invention, can be of any functional geometrical shape. It is also noted that it is possible to affix alternative embodiments of the present invention bioelectric interface to the back of a subject as well as to the chest thereof.

It is also noted that primary evidence that a Wilson Central Terminal (WCT) Voltage produced utilizing a present invention Bioelectric Interface is equivalent, (eg. within some selected range of deviation from), to that produced when conventionally placed limb leads are utilized, is essential equivalence of monitored ECC lead outputs from both said systems. In that light it is to be understood that a conventional Wilson Central Terminal is constructed utilizing resistors of equal value, (eg. 10,000 to 100,000 ohms each). Again refering to FIGS. 6a and 6b, this is equivalent to considering Resistors (r1), (r2) and (r3) to be of equivalent values. Where this is the case, placement of the Right Arm (RA), Left Arm (LA) and Left Leg (LL) electrodes alone, in a FIG. 6b setting, provides for realizing a voltage at the FIG. 6b Wilson Central Terminal (WCT) which is in a desired relationship to that present at the Wilson Central Terminal (WCT) formed utilizing electrodes positioned on limbs, as shown in FIG. 6a. However, it should be appreciated that if resistors/summing impedances (r1), (r2) and (r3) are variable, then adjusting their values can also have an effect on the voltage which appears at a Wilson Central Terminal (WCT). The present invention provides for use of variable (r1) and/or (r2) and/or (r3) resistor(s) such that in use, adjustment of one or more of said variable (r1) and/or (r2) and/or (r3) resistor(s) allows "setting" a voltage at the Wilson Central Terminal (WCT) to essentially any value at, or anywhere between, the voltages present at any of the Right Arm (RA), Left Arm (LA) and Left Leg (LL) electrodes. Thus, the present invention can include as a Method of Use step, adjustment of the values of the resistors which form the Wilson Central Terminal (WCT), after a FIG. 6b Bioelectric Interface (3) is placed upon a subject's chest. (Note that Operational Amplifiers with adjustable gain can be utilized in place of the described variable resistors and are to be considered functionally equivalent and within the scope of the terminology "variable resistor". Op-Amps beneficially provide high input impedance.)

It will be apparent to those skilled in the art that some redundancy exists in any Einthoven-like lead system which lies largely in a single subject body plane, such as the frontal plane some minor efficiencies might be achieved, at the expense of redundancy, if for example, two mutually perpendicular leads were created and used exclusively to define the frontal plane in electrocardiology. Furthermore, other mathematically derived leads are commonly employed to provide reconfigured information, (eg "augmented" frontal plane leads). However, it is to be understood that uncorrelated heart related information can not be created simply by the mathematical manipulation of redundant information. Therefore, where appropriate, this disclosure is to be interpreted to include mathematically equivalent lead placement systems. In particular, the language, "generally in the region of" should be interpreted sufficiently broadly to include both an Einthoven equivalent triangle and an orthogonal lead configuration formed by a shifting of a lead position, which identified lead configurations provide mathematically essentially equivalent information.

It is specifically stated, as it is difficult to otherwise describe, that for the purposes of this disclosure the term "undulate" is defined as indicating a sequential plurality of curves in said bioelectric interface "undulated" outer perimeter boundary (UOPB), as shown in FIGS. 7e and 7f. This is best understood by comparison to a bioelectric interface outer perimeter boundary with a relatively "smoothed" shape, as is shown in FIGS. 7a–7d.

In keeping with the Method theme of the present invention as described in the Disclosure of the Invention Section herein, FIG. 8a generally exemplifies a system for utilizing an electrode patch (3) as shown in FIGS. 7a–7f. A computer system is shown situated to receive subject (ECG) and Upper Torso Impedance Interrrogation signals, and based thereupon cause a control system identified as (PACE/DEFIB) to provide electrical impulses to a subject via said electrode patch (3). The (PACE/DEFIB) control system provides logic, voltage and switchable impedance source means to perform the method recited in the Disclosure of the Invention Section of this Specification. Specifically, it is to be appreciated that resistors can be attached to any of the RA, LA, LL, V1, V2, V3, V4, V5, V6 electrodes via said (PACE/DEFIB) control system, for the purpose of applying controlled theraputic voltages therethrough, in use.

Figure 9A:
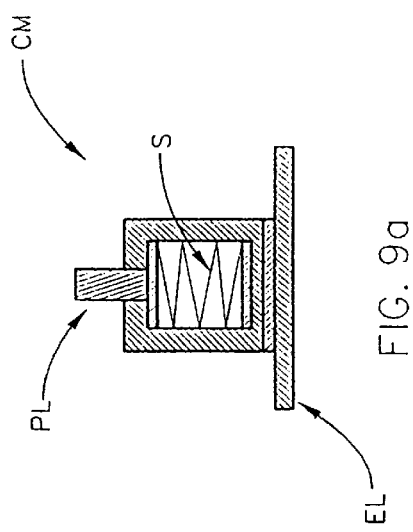
FIGS. 9a and 9b show defibrillation paddle electrical contact enhancing spring-loaded piston type electrode contact means.
Figure 9B:
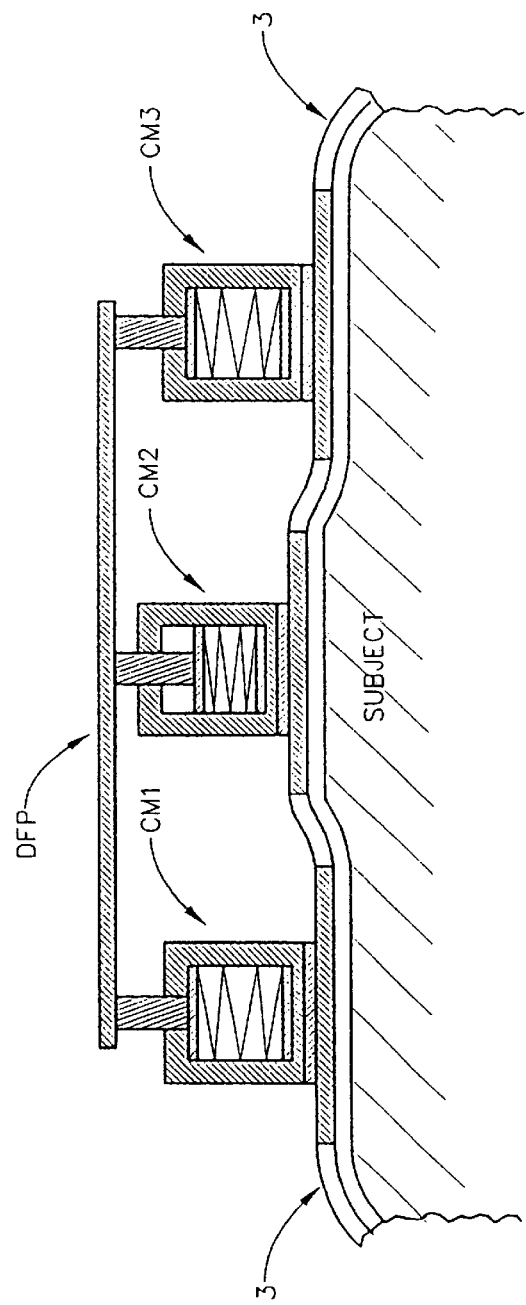

It is further noted that where FIG. 7d Defibrillation Paddles ((DF1) and (DF2) in FIG. 7d) are placed in contact with groups of electrodes, and it can happen that electrodes can be project to different heights above an OMNITRODE (3) when it is placed on a subject, (see FIG. 9b). FIG. 9a shows that an Electrode (CM) above a Subject Contacting aspect (EL) can be constucted to include Spring Means (S) with a Piston-type (P) contact present at an upper aspect. FIG. 9b shows the electrical contact enhancing action of a plurality of such Electrodes (CM1), (CM2) and (CM3) when a Defibrillation Paddle (DFP) is simultaneously placed thereonto. Thus, the present invention includes FIGS. 9a and 9b electrode contacting enhancing means.

Finally, it is to be understood that 12 lead ECG data can be acquired from all electrodes simultaneously or sequentally, and either approach is within the scope of the present invention.

Having hereby disclosed the subject matter of the present invention, it should be obvious that many modifications, substitutions, and variations of the present teachings are possible in view of the teachings. It is therefore to be understood that the present invention may be practiced other than as specifically described, and should be limited in breadth and scope only by the Claims.

I claim:

1. A bioelectric interface comprising at least two defibrillation electrodes as an integral part thereof, there being perforations, or functional equivalent, in said bioelectric interface, positioned to allow easy detachment of at least one of said defibrillation electrodes, said bioelectric interface further comprising sufficient precordial electrodes to monitor twelve lead ECG's.

2. A bioelectric interface as in claim 1, in which
   the defibrillation electrodes have affixed thereto electrodes appropriate for use as right-arm and left-leg limb electrodes; or
   the defibrillation electrodes are used for both defibrillation and as right arm and left leg limb electrodes.

3. A bioelectric interface as in claim 1, which further comprises ECG limb lead forming electrodes (RA) (LA) and (LL) configured in an RA, LA, LL electrocardiogram system electrode pattern; said defibrillation electrodes optionally being said (RA) and (LL) limb electrodes; which RA, LA and LL electrodes, when functionally combined with summing impedances from each thereof, which summing impedances are "Y" interconnected to provide a Wilson central terminal, form an Einthoven frontal lead triangle with a I, II, III lead pattern when mounted to a subject's chest, said Einthoven frontal lead triangle with a I, II, III lead pattern being positioned on said subject's chest so as to provide a voltage which presents at said Wilson central terminal which is within a selected range of deviation from a voltage which would appear at a Wilson central terminal formed from summing impedances from conventional limb mounted electrodes which are "Y" interconnected;
   said (RA) and (LL) each being a selection from the group consisting of:
       one of the defibrillation electrodes; and
       an electrode other than one of the defibrillation electrodes.

4. A bioelectric interface as in claim 1, which further comprises six precordial V1, V2, V3, V4, V5 and V6, and three limb RA, LA and LL lead electrodes located in regions as:
   electrode region RA generally in the region of the first or second intercostal space to the right of the sternum;
   electrode region LA generally in the region of the left third or fourth intercostal space at the mid-axillary line;
   electrode region LL generally in the region of the inferior costal margin in the left mid-clavicular line;
   electrode region V1 in the region of the fourth intercostal space at the right sternal border;
   electrode region V2 in the region of the fourth intercostal space at the left sternal border;
   electrode region V4 in the region of the fifth intercostal space at the left mid-clavicular line;
   electrode region V3 in the region of the midpoint between electrode regions V2 and V4;
   electrode region V5 in the region of the fifth intercostal space in the left anterior axillary line; and
   electrode region V6 in the region of the fifth intercostal space in the mid-axillary line.

5. A bioelectric interface comprising a carrier matrix in functional combination with at least two spatially separated defibrillation electrodes, and V1, V2, V3, V4, V5, and V6 precordial electrodes and RA, LA and LL limb lead forming electrodes, said electrodes being affixed to said carrier matrix in a manner such that their relative positions with respect to one another are essentially fixed, said RA, LA, LL limb lead electrodes being positioned such that when functionally combined with summing impedances from each thereof, which summing impedances are "Y" interconnected to provide a Wilson central terminal, form an Einthoven frontal lead triangle with a I, II, III lead pattern when mounted to a subject's chest, said Einthoven frontal lead triangle with a I, II, III lead pattern being positioned on said subject's chest so as to provide a voltage which presents at said Wilson central terminal which is within some selected range of deviation from a voltage which would appear at a Wilson central terminal formed from summing impedances from conventional limb mounted electrodes which are "Y" interconnected;
   the improvement being that there are perforations, or functional equivalent, in said bioelectric interface, positioned to allow easy detachment of at least one of said spatially separated defibrillation electrodes.

6. A bioelectric interface as in claim 5, which further comprises an adhesive comprised of electrically conductive polymer affixed to said carrier matrix on a side thereof which contacts said subject's chest in use.

7. A bioelectric interface as in claim 6, in which the electrically conductive polymer is hydrophillic, and thereby particularly well suited for application to human skin.

8. A bioelectric interface as in claim 6, in which the defibrillation electrodes, and V1, V2, V3, V4, V5, and V6 precordial electrodes and RA, LA and LL limb lead forming electrodes, are each of a construction such that contact with the adhesive is essentially continuous over the dimension of each said electrode.

9. A bioelectric interface as in claim 6, in which at least one of said electrodes is of a multiple-piece construction such that each of said multiple pieces contacts the adhesive independently and essentially continuously over the dimension of each said multiple pieces.

10. A bioelectric interface as in claim 9, in which the multipiece construction configures a Bulls-eye pattern.

11. A bioelectric interface as in claim 5, which further comprises an adhesive sheet affixed thereto so as to sandwich said electrodes between said carrier matrix and said adhesive sheet, the purpose being to improve subject adherence.

12. A bioelectric interface as in claim 5, which further comprises means for electrically connecting said electrodes to external devices.

13. A bioelectric interface as in claim 5, in which there are present a multiplicity of electrodes configured in an essentially rectangular shaped matrix such that in use said bioelectric interface is affixed to a subject's chest or back, said bioelectric interface being appropriate for use in electrocardiographic mapping.

14. A bioelectric interface as in claim 5, in which there are present a multiplicity of electrodes configured in an RA, LA, LL, V1, V2, V3, V4, V5, V6 twelve lead electrocardiogram system electrode pattern, such that nine regions of electrode (s) are positioned on a subject's chest during use.

15. A bioelectric interface comprising an adhesive sheet in functional combination with at least two spatially separated regions of defibrillation electrode(s), at least one of which spatially separated region of defibrillation electrode(s) can consist of more than one electrode, which adhesive sheet simultaneously presents with essentially anisotropic specific impedance properties and essentially isotropic pliability and adhesion mechanical properties, electrode(s) in each of said spatially separated regions of electrode(s) being affixed to said adhesive sheet in a manner such the relative positions of electrodes present with respect to one another are essentially fixed, and such that the specific impedance from each electrode in said regions of spatially separated electrode(s) directly through the thickness of said adhesive sheet, is less than that between any two electrodes in different spatially separated regions of electrode(s) through said adhesive sheet, said electrical anisotropic specific impedance properties of said adhesive sheet being the result of scrim therein, which scrim is a web of material with relatively electrically conductive adhesive material present in open areas of said web so as to form channel regions of electrically conductive adhesive material bordered by said scrim material, such that adhesive material in one channel region does not contact that in other regions; and/or slits therein, which slits are positioned between electrodes;

there being perforations, or functional equivalent, in said bioelectric interface, positioned to allow easy detachment of at least one of said spatially separated defibrillation electrodes.

16. A bioelectric interface as in claim 15, in which the adhesive sheet is comprised of electrically conductive polymer.

17. A bioelectric interface as in claim 16, in which the electrically conductive polymer is hydrophillic, and thereby particularly well suited for application to human skin.

18. A bioelectric interface as in claim 15, in which the electrodes in the regions of electrode(s) are each of a construction such that contact with the adhesive sheet is essentially continuous over the dimension of each said electrode.

19. A bioelectric interface as in claim 15, in which at least one of said electrodes in said regions of electrode(s) is of a multiple-piece construction such that each of said multiple pieces contacts the adhesive sheet independently and essentially continuously over the dimension of each said multiple pieces.

20. A bioelectric interface as in claim 19, in which the multipiece construction configures a Bulls-eye pattern.

21. A bioelectric interface as in claim 15, which further comprises a carrier matrix affixed thereto so as to sandwich said electrodes in said regions of electrode(s) between said carrier matrix and said adhesive sheet, the purpose being to improve the integrity of the spatial separation between said electrodes.

22. A bioelectric interface as in claim 15, which further comprises means for electrically connecting said electrodes in said regions of electrodes to external devices.

23. A bioelectric interface as in claim 15, which further comprises at least three additional regions of electrodes, said bioelectric interface being configured and sized so as to place said three regions of electrodes in an essentially congruent Einthoven triangle Left Arm, Right Arm, Left Leg pattern, such that in use all said regions of electrodes contact a subject's chest.

24. A bioelectric interface as in claim 15, which further comprises at least nine regions of electrode(s) being configured in an RA, LA, LL, V1, V2, V3, V4, V5, V6 twelve lead electrocardiogram system electrode pattern, such that said nine regions of electrode(s) are positioned on a subject's chest during use as follows:

electrode region RA generally in the region of the first or second intercostal space to the right of the sternum;
electrode region LA generally in the region of the left third or fourth intercostal space at the mid-axillary line;
electrode region LL generally in the region of the inferior costal margin in the left mid-clavicular line;
electrode region V1 in the region of the fourth intercostal space at the right sternal border;
electrode region V2 in the region of the fourth intercostal space at the left sternal border;
electrode region V4 in the region of the fifth intercostal space at the left mid-clavicular line;
electrode region V3 in the region of the midpoint between electrode regions V2 and V4;
electrode region V5 in the region of the fifth intercostal space in the left anterior axillary line; and
electrode region V6 in the region of the fifth intercostal space in the mid-axillary line.

25. A bioelectric interface as in claim 15, which further comprises at least three regions of electrode(s) which are configured and sized so as to place electrode(s) in said three regions of electrodes in an Einthoven triangle Left Arm, Right Arm, Left Leg pattern, such that in use all said regions of electrodes contact a subject's chest as verified by the appearance of a voltage at a Wilson central terminal formed by attaching summing impedances from electrodes in each of said three regions of electrode(s) in a "Y" configuration which is within some selected deviation from a voltage which would appear at a Wilson central terminal formed by attaching summing impedances from electrodes affixed to conventional RA, LA and LL into a "Y" configuration.

26. A method of defibrilating a subject comprising the steps of:
  a. providing a bioelectric interface comprising an adhesive sheet in functional combination with at least two spatially separated regions of defibrillation electrodes, at least one of which spatially separated region of defibrillation electrode(s) can consist of more than one electrode, there being perforations, or functional equivalent, in said bioelectric interface, positioned to allow easy detachment of at least one of said spatially separated regions of defibrilation electrodes, which adhesive sheet presents with essentially anisotropic specific impedance properties but essentially isotropic mechanical properties, said spatially separated regions of defibrillation electrode(s) being affixed to said adhesive sheet in a manner such that their relative positions with respect to one another remain essentially fixed, and such that the specific impedance from each electrode in said regions of spatially separated defibrillation electrode(s) directly through the thickness of said adhesive sheet, is less than that between any two electrodes in different spatially separated regions of said defibrillation electrodes through said adhesive sheet, said electrical anisotropic specific impedance properties of said adhesive sheet being the result of:
    scrim therein, which scrim is a web of material with relatively electrically conductive adhesive material present in open areas of said web so as to form channel regions of electrically conductive adhesive material bordered by said scrim material, such that adhesive material in one channel region does not contact that in other regions; and/or
    slits therein, which slits are positioned between electrodes;
    in which bioelectric interface the number of regions of electrode(s) is at least nine, nine of said at least nine regions of electrode(s) being configured in an RA, LA, LL, V1, V2, V3, V4, V5, V6 twelve lead electrocardiogram system electrode pattern, such that said nine regions of electrode(s) are positioned on a subject's chest during use as follows:

electrode region RA generally in the region of the first or second intercostal space to the right of the sternum;

electrode region LA generally in the region of the left third or fourth intercostal space at the mid-axillary line;

electrode region LL generally in the region of the inferior costal margin in the left mid-clavicular line;

electrode region V1 in the region of the fourth intercostal space at the right sternal border;

electrode region V2 in the region of the fourth intercostal space at the left sternal border;

electrode region V4 in the region of the fifth intercostal space at the left mid-clavicular line;

electrode region V3 in the region of the midpoint between electrode regions V2 and V4;

electrode region V5 in the region of the fifth intercostal space in the left anterior axillary line; and electrode region V6 in the region of the fifth intercostal space in the mid-axillary line;

b. affixing said bioelectric interface to a subject and causing the defibrillation electrodes therein to be electrically attached to a defibrillation system and applying a defibrilating shock therewith through said defibrillation electrodes.

27. A method of defibrilating a subject as in claim 14, which further comprises the step of performing a procedure selected from the group consisting of;

a. cardio-pulmonary resuscitation b. ECG monitoring;

c. cardiac pacing;

d. electro surgery;

e. electro-ablation;

f. impedance cardiography;

g. transdermal drug or nutrient transfer; and h. electromechanical energy transfer or detection;

on said subject without removing said bioelectric interface.

28. A method of defibrilating a subject as in claim 26, which further comprises the simultaneously step of causing at least some some of said electrodes to have a multiple component configuration.

29. A method of performing defibrillation comprising the steps of:

a. providing a bioelectric interface comprising an adhesive sheet in functional combination with at l-east two spatially separated defibrillation electrodes, there being perforations, or functional equivalent, in said bioelectric interface, positioned to allow easy detachment of at least one of said spatially separated defibrilation electrodes, which adhesive sheet presents with essentially anisotropic specific impedance properties but essentially isotropic mechanical properties, said defibrialtion electrodes being affixed to said adhesive sheet in a manner such that their relative positions with respect to one another remain essentially fixed, and such that the specific impedance from each said electrode directly through the thickness of said adhesive sheet, is less than that between any two of said electrodes through said adhesive sheet;

b. affixing said bioelectric interface to a subject's chest or back, and causing said defibrillation electrodes to be connected to a defibrillation system and causing said defibrillation system to deliver a defibrillation shock therethrough.

30. A method of performing defibrillation claim 29, which further comprises the step of performing a procedure selected from the group consisting of;

a. cardiopulmonary resuscitation b. ECG monitoring;

c. cardiac pacing;

d. electro surgery;

e. electro-ablation;

f. impedance cardiography;

g. transdermal drug or nutrient transfer; and h. electromechanical energy transfer or detection.

31. A method of performing defibrillation as in claim 29, which further comprises the simultaneous step of causing at least some of said electrodes to have a multiple component configuration.

32. A bioelectric interface comprising a support sheet to which are affixed at least two (2) defibrillation electrodes, in functional combination with at least three (3) spatially separated electrocardiogram system electrodes, each of said at least three (3) spatially separated electrocardiogram system electrodes being of a construction selected from the group consisting of:

a single electrical electrode element; and a group of electrically independent electrode elements;

each of said spatially separated electrocardiogram system electrodes being affixed to said support sheet in a manner such that the relative positions of said electrocardiogram system electrodes with respect to one another are essentially fixed therewithin, three (3) of said at least three (3) electrocardiogram system electrodes being configured in an RA, LA, LL electrocardiogram system electrode pattern; which RA, LA and LL electrodes, when functionally combined with summing impedances from each thereof, which summing impedances are "Y" interconnected to provide a Wilson central terminal, form an Einthoven frontal lead triangle with a I, II, III lead pattern when mounted to a subject's chest, said Einthoven frontal lead triangle with a I, II, III lead pattern being positioned on said subject's chest so as to provide a voltage which presents at said Wilson central terminal which is within some selected range of deviation from a voltage which would appear at a Wilson central terminal formed from summing impedances from conventional limb mounted electrodes which are "Y" interconnected;

said bioelectric interface further comprising:

a. an adhesive sheet is affixed to said support sheet on a subject contacting side thereof and simultaneously presents with essentially anisotropic impedance properties and essentially isotropic mechanical pliability and adhesion properties, said electrodes being affixed to said adhesive sheet such that the impedance from each said electrode directly through the thickness of said adhesive sheet, is less than that between any two of said electrodes through said adhesive sheet; and/or b. perforations are present in said support sheet which allow easy detachment and deployment of at least one of said Einthoven frontal lead triangle RA, LA and LL electrodes, so that said at least one of said Einthoven triangle RA, LA, and LL electrodes is/are, in use, positionable at locations selected from the group consisting of:
  in contact with a subject's chest; and
  in conventional Einthoven triangle forming subject limb positions; and/or
c. an undulated outer edge on said bioelectric interface support sheet; and/or
d. at least one hole through said bioelectric interface support sheet which allows access to the skin of a subject to which it is affixed in use;

there being perforations, or functional equivalent, in said bioelectric interface, positioned to allow easy detachment of at least one of said spatially separated defibrillation electrodes.

33. A bioelectric interface as in claim 32 wherein at least one of said RA, LA and LL electrodes, when mounted to a subject's chest, is positioned as:
  said electrode RA being generally in the region of the first second intercostal space to the right of the sternum;
  said electrode LA being generally in the region of the left third or fourth intercostal space in the mid-axillary line;
  said electrode LL being generally in the region of the inferior costal margin in the left mid-clavicular line.

34. A bioelectric interface as in claim 32 which comprises said RA, LA, LL electrodes, and further comprises V1, V2, V3, V4, V5, V6 twelve lead electrocardiogram system electrode pattern, such that said electrode(s) are positioned on a subject's chest during use as follows:
  electrode region RA generally in the region of the first or second intercostal space to the right of the sternum;
  electrode region LA generally in the region of the left third or fourth intercostal space at the mid-axillary line;
  electrode region LL generally in the region of the inferior costal margin in the left mid-clavicular line;
  electrode region V1 in the region of the fourth intercostal space at the right sternal border;
  electrode region V2 in the region of the fourth intercostal space at the left sternal border;
  electrode region V4 in the region of the fifth intercostal space at the left mid-clavicular line;
  electrode region V3 in the region of the midpoint between electrode regions V2 and V4;
  electrode region V5 in the region of the fifth intercostal space in the left anterior axillary line; and
  electrode region V6 in the region of the fifth intercostal space in the mid-axillary line.

35. A bioelectric interface as in claim 32, in which is present at least one hole through said bioelectric interface support sheet which allows access to the skin of a subject to which it is affixed in use, one of said said at least one hole(s) being oriented so as to allow access to the sternum process of a subject to which said bioelectric interface is applied in use.

36. A bioelectric interface as in claim 32, which is further characterized by:
  a. an adhesive sheet is affixed to said support sheet on a subject contacting side thereof and simultaneously presents with essentially anisotropic impedance properties and essentially isotropic mechanical pliability and adhesion properties, said electrodes being affixed to said adhesive sheet such that the impedance from each said electrode directly through the thickness of said adhesive sheet, is less than that between any two of said electrodes through said adhesive sheet; and/or
  b. perforations in said support sheet which allow easy detachment and deployment of at least one of said Einthoven frontal lead triangle RA, LA and LL electrodes, so that said at least one of said Einthoven triangle RA, LA, and LL electrodes is/are, in use, positionable at locations selected from the group consisting of:
    in contact with a subject's chest; and
    in conventional Einthoven triangle forming subject limb positions; and/or
  c. an undulated outer edge on said bioelectric interface support sheet; and/or
  d. at least one hole through said bioelectric interface support sheet which allows access to the skin of a subject to which it is affixed in use.

37. A bioelectric interface as in claim 32, which is further characterized by:
  a. at least one said electrocardiogram system electrode which comprises spring-loaded means on a non-subject contacting side thereof, which spring-loaded means develops compression derived force when caused to be compressed, the purpose thereof being to facilitate electrical contact to an electrically conductive element caused to be placed in contact therewith in use, by development of said compression derived force.

38. A bioelectric interface as in claim 32, in which at least one of said at least three (3) spatially separated electrocardiogram system electrodes is of a construction such that there is present a "cocklebur-like" structure means at a subject contacting side thereof, said "cocklebur-like" structure means serving to effect improved electrical contact to a subject in use.

39. A bioelectric interface comprising at least two defibrillation electrodes as an integral part thereof, at least one of which defibrillation electrode(s) can consist of more than one electrode, said at least two defibrillation electrodes being affixed in an adhesive sheet which simultaneously presents with essentially anisotropic specific impedance properties and essentially isotropic pliability and adhesion mechanical properties, said at least two electrode(s) being spatially separated and affixed to said adhesive sheet in a manner such the relative positions of electrodes present with respect to one another are essentially fixed, and such that the specific impedance between said electrodes through said adhesive sheet, is greater than that straight through said adhesive sheet;
  the improvement being that there are perforations, or functional equivalent, in said bioelectric interface, positioned to allow easy detachment of at least one of said defibrillation electrodes from the other of said at least two defibrillation electrodes.

40. A bioelectric interface comprising two defibrillation electrodes as an integral part thereof as in claim 39, said bioelectric interface further comprising sufficient precordial electrodes to monitor twelve lead ECG's.

41. A bioelectric interface comprising two defibrillation electodes as in claim 40, which further comprises an ECG monitor system to which said precordial electrodes are connected.

42. A bioelectric interface as in claim 39, in which two of the at least two defibrillation electrodes have affixed thereto electrodes appropriate for use in forming right-arm (RA) and left-leg (LL) limb leads.

43. A bioelectric interface as in claim 39, which further comprises a (RA) ECG limb lead forming electrode, which in combination with two of said at least two defibrillation electrodes which are positioned appropriately to serve as LA and LL electrodes, forms an RA, LA, LL electrocardiogram system electrode pattern, which RA, LA and LL electrodes, when functionally combined with summing impedances from each thereof, which summing impedances are "Y" interconnected to provide a Wilson central terminal, form an Einthoven frontal lead triangle with a I, II, III lead pattern when mounted to a subject's chest.

44. A bioelectric interface comprising two defibrillation electrodes as in claim 43, which further comprises an ECG monitor system to which said limb lead electrodes are connected.

45. A bioelectric interface as in claim 39, which further comprises a harness thereon to which is affixed, in use, a bundle of wires, said bundle of wires providing separate electrical contact to said at least two defibrillation electrodes.

46. A bioelectric interface comprising two defibrillation electrodes as in claim 39, which further comprises a source of defibrillation shock energy to which said two defibrillation electodes are connected.

47. A combination of two defibrillation electrodes and a bioelectric interface which comprises a support sheet in which are affixed sufficient precordial and limb lead forming electrodes to enable twelve lead ECG monitoring, said bioelectric interface having an undulated outer edge, the shape of which substantially matches the shape of said defibrillation electrodes along a locus at which said bioelectric interface and said defibrillation electrodes closely mate to one another.

48. A combination of two defibrillation electrodes and a bioelectric interface as in claim 47, in which the support sheet has at least one hole therein.

* * * * *